United States Patent
Ashworth et al.

[11] Patent Number: 5,935,955
[45] Date of Patent: *Aug. 10, 1999

[54] PHARMACEUTICAL PIPERAZINE COMPOUNDS

[75] Inventors: Philip A. Ashworth; Sukhjit Hunjan; Ian A. Pretswell; Harnish Ryder, all of Slough, United Kingdom; Stephen J. Brocchini, Highland Park, N.J.

[73] Assignee: Xenova Limited, Berkshire, United Kingdom

[ * ] Notice: This patent is subject to a terminal disclaimer.

[21] Appl. No.: 08/860,328
[22] PCT Filed: Dec. 22, 1995
[86] PCT No.: PCT/GB95/03029
§ 371 Date: Aug. 29, 1997
§ 102(e) Date: Aug. 29, 1997
[87] PCT Pub. No.: WO96/20180
PCT Pub. Date: Jul. 4, 1996

[30] Foreign Application Priority Data
Dec. 23, 1994 [GB] United Kingdom ................... 9426090

[51] Int. Cl.$^6$ ...................... A61K 31/495; C07D 241/02; C07D 401/12; C07D 403/14
[52] U.S. Cl. ...................... 514/235.8; 514/252; 514/253; 514/255; 544/121; 544/295; 544/357; 544/360; 544/361; 544/363; 544/385
[58] Field of Search ................................... 544/385, 121, 544/357, 295, 360, 361, 363; 514/252, 253, 255, 235.8

[56] References Cited

U.S. PATENT DOCUMENTS 5,700,804  12/1997  Collins et al. ........................ 514/255
5,750,530   5/1998  Bryans et al. ........................ 544/360

FOREIGN PATENT DOCUMENTS

WO 94/01408  1/1994  WIPO .
WO 94/04512  3/1994  WIPO .
WO 94/04513  3/1994  WIPO .
95 21832     8/1995  WIPO .

OTHER PUBLICATIONS

Bellamy et al, Cancer Investigations 8 pp. 547–562, 1990.
Hill, International Journal of Oncology 9 197–203 1996 "Drug Resistance: An overview of the current state of the art".
Dale et al, British J. of Cancer (1998) 78 (7), 885 to 892 Reversal of P–glycoprotein–mediated multidrug etc.
Germann, European J. of Cancer vol. 32 A, No. 6, pp. 927–944, 1996 "P–glycoprotein—A Mediator of Multidrug Resistance in Tumour Cells".
British Journal of Cancer (1997), 75 (suppl 1), abstracts 1.8 and P58 of two posters by Tuffley et al and Mistry et al.
Annals of Oncology 7 (suppl. 1) Mar. 1996, No. 434, Luscombe et al.
Ann. Rev. of Biochemistry 62 (1993) 385–427: Gottesman et al.
Prospectus for the public offering of shares in Xenova Limited Dec. 19, 1996 (cover, inside sheet and p. 51) by Xenova Limited.

*Primary Examiner*—Emily Bernhardt
*Attorney, Agent, or Firm*—Nixon & Vanderhye P.C.

[57] ABSTRACT

A piperazinedione of general formula (I):

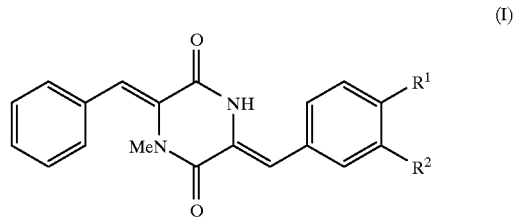

(I)

wherein $R^1$ is selected from
hydrogen;
a group of formula $-(NH)_t-COR^3$ wherein t is 0 or 1 and $R^3$ is an organic substituent as defined herein;
a group of formula (D):

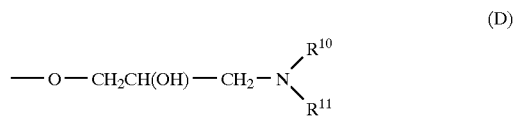

(D)

and
a group of formula (E):

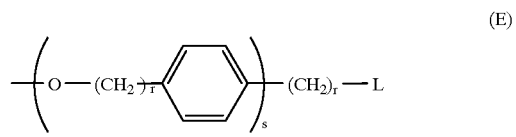

(E)

and the pharmaceutically acceptable salts thereof are useful as modulators of multi-drug resistance.

18 Claims, No Drawings

PHARMACEUTICAL PIPERAZINE COMPOUNDS

The present invention relates to compounds useful as modulators of multi-drug resistance (MDR), to their preparation and to pharmaceutical and veterinary compositions containing them.

The resistance of tumours to treatment with certain cytotoxic agents is an obstacle to the successful chemotherapeutic treatment of cancer patients. A tumour may acquire resistance to a cytotoxic agent used in a previous treatment. A tumour may also manifest intrinsic resistance, or cross-resistance, to a cytotoxic agent to which it has not previously been exposed, that agent being unrelated by structure or mechanism of action to any agent used in previous treatments of the tumour.

Analogously, certain pathogens may acquire resistance to pharmaceutical agents used in previous treatments of the diseases or disorders to which those pathogens give rise. Pathogens may also manifest intrinsic resistance, or cross resistance, to pharmaceutical agents to which they have not previously been exposed. Examples of this effect include multi-drug resistant forms of malaria, tuberculosis, leishmaniasis and amoebic dysentery.

The above phenomena are referred to collectively as multi-drug resistance (MDR). As discussed more fully later on, a plasma membrane glycoprotein (P-gp) is implicated in the mechanism which underlies MDR. P-gp has drug binding properties. Certain agents which have the capacity to modulate MDR may therefore also be useful in facilitating the delivery of drugs across the blood-brain barrier and in treating AIDS and AIDS-related complex.

Disadvantages of drugs which have so far been used to modulate MDR, termed resistance modifying agents or RMAs, are that they frequently possess a poor pharmacokinetic profile and/or are toxic at the concentrations required for MDR modulation.

It has now been found that a series of piperazinedione derivatives have activity as modulators of multi-drug resistance. The present invention therefore provides a piperazinedione derivative of formula (I):

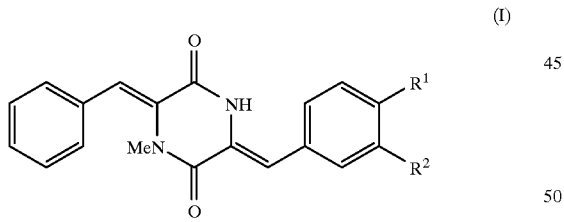

(I)

wherein $R^1$ is selected from:
hydrogen;
a group of formula $-(NH)_t-COR^3$ wherein t is 0 or 1 and $R^3$ is selected from:

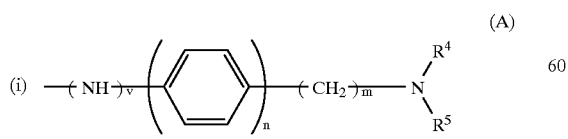

(A)

wherein v is 0 when t is 1 and v is 1 when t is 0; and wherein n is 0 or 1 and m is 0, 1, 2 or 3, at least one of n and m being other than 0, and either:

(a) $R^4$ is H or $C_1-C_6$ alkyl and $R^5$ is $C_1-C_6$ alkyl optionally substituted by one or two phenyl groups, the phenyl group or groups being optionally substituted by one or two $C_1-C_6$ alkoxy groups; or
(b) $R^4$ and $R^5$, together with the nitrogen atom to which they are attached, form a heterocyclic group selected from (1) to (4):

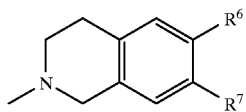
(1)

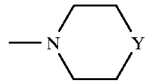
(2)

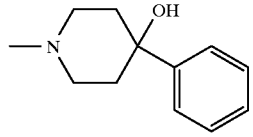
(3)

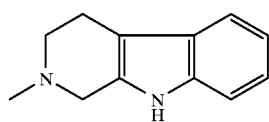
(4)

wherein $R^6$ and $R^7$, which are the same or different, are H or $C_1-C_6$ alkoxy or $R^6$ and $R^7$ form together a methylenedioxy group; Y is O or $-NR^8$ wherein $R^8$ is $C_1-C_6$, alkyl or a phenyl group optionally substituted by $CF_3$;

$$-NH-(CH_2)_p-Z \quad (B)$$

wherein p is 1 or 2 and Z is $C_2-C_6$ alkenyl or a phenyl group optionally substituted by $C_1-C_6$ alkoxy; and (C)

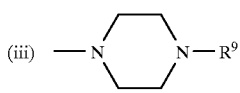
(iii)

wherein $R^9$ is $C_1-C_6$ alkyl, pyrimidinyl or a phenyl group optionally substituted by $C_1-C_6$ alkoxy; and (F)

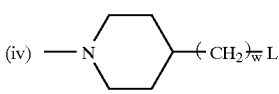
(iv)

wherein w is 1, 2 or 3 and L is a heterocyclic group of formula (1) as defined above;

a group of the formula (D):

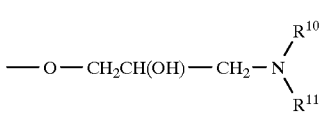

(D)

wherein each of $R^{10}$ and $R^{11}$, which may be the same or different, is $C_1$–$C_6$ alkyl; and
a group of formula (E):

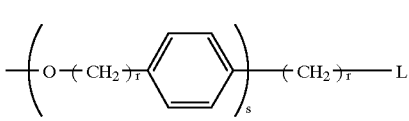

(E)

wherein s is 0 or 1 and each r, which may be the same or different, is 1, 2 or 3 and L is a heterocyclic group of formula (1) as defined above;
and $R^2$ is hydrogen or a group of formula —$COR^3$ as defined above provided that one of $R^1$ and $R^2$ is hydrogen and the other is not hydrogen; or a pharmaceutically acceptable salt thereof.

An alkyl group may be linear or branched. A $C_1$–$C_6$ alkyl group is typically a $C_1$–$C_4$ alkyl group, for example a methyl, ethyl, propyl, i-propyl, n-butyl, sec-butyl or tert-butyl group. A $C_1$–$C_6$ alkoxy group is typically a $C_1$–$C_4$ alkoxy group, for example a methoxy, ethoxy, propoxy, i-propoxy, n-butoxy, sec-butoxy or tert-butoxy group.

When $R^1$ is a group of formula —$(NH)_t$—$COR^3$, t may be 0 in which case the group has the formula —$COR^3$. The integer v in formula (A) is then 1. When $R^3$ is a group of formula (A), n is typically 1 and m is 0, 1, 2 or 3, or n is 0 and m is 2. $R^4$ and $R^5$ may be as defined under (a), in which case $R^4$ is preferably $C_1$–$C_6$ alkyl, for instance methyl. $R^5$ is preferably $C_1$–$C_6$ alkyl, for instance methyl or ethyl, either unsubstituted or substituted on the terminal carbon atom by one or two phenyl groups. These phenyl groups are in turn unsubstituted or substituted by one or two methoxy groups. For instance, $R^5$ may be a diphenylmethyl, 2-2-diphenylethyl or 3,4-dimethoxyphenethyl group. Alternatively, $R^4$ and $R^5$ may be as defined under (b). When $R^4$ and $R^5$ together form the heterocyclic ring (1), $R^6$ and $R^7$ are typically the same, and are preferably hydrogen or methoxy, or together form a methylenedioxy group. When $R^4$ and $R^5$ together form the heterocyclic ring (2), Y is O or —$NR^8$ wherein $R^8$ is preferably methyl, phenyl or 3-trifluoromethylphenyl.

When $R^3$ is a group of formula (B), Z is preferably ethenyl, prop-1-enyl or prop-2-enyl, or a phenyl group substituted by one or two $C_1$–$C_6$ alkoxy groups, preferably methoxy groups. Preferably the phenyl ring is 3,4-disubstituted by methoxy groups.

When $R^3$ is a group of formula (C), $R^9$ is preferably selected from methyl, ethyl, pyrimidinyl and phenyl, the phenyl being monosubstituted at position 2, 3 or 4 by $C_1$–$C_6$ alkoxy, for instance methoxy, and more preferably being a 4-methoxyphenyl group.

When $R^1$ is a group of formula (D) $R^{10}$ and $R^{11}$ are typically the same and are preferably both methyl. When $R^1$ is a group of formula (E), s may be 0 in which case the group has the formula —$(CH_2)_r$—L. In formula (E) the substituents $R^6$ and $R^7$ in the heterocyclic ring are typically the same and are preferably both H or methoxy, or together form a methylenedioxy group.

In a first embodiment of formula (I) in which t=1 and v=0, $R^1$ is hydrogen and $R^2$ is a group of formula —$COR^3$ as defined above in which $R^3$ is a group of formula A.

In a second embodiment of formula (I) $R^2$ is hydrogen and $R^1$ is a group of formula —$COR^3$ as defined above in which $R^3$ is a group of formula (A), a group of formula (B) wherein Z is ethenyl or phenyl substituted by two $C_1$–$C_6$ alkoxy groups, or a group of formula (C) wherein $R^2$ is methyl, pyrimidinyl or phenyl. Phenyl substituted by two $C_1$–$C_6$ alkoxy groups is preferably 3,4-dimethoxyphenyl.

In formula (A) in the first and second embodiments described above it is preferred that n is 0 and m is 2, or n is 1 and m=0, 1 or 2, and either:
(a) $R^4$ is $C_1$–$C_6$ alkyl and $R^5$ is $C_1$–$C_6$ alkyl substituted on the terminal C atom by 2 unsubstituted phenyl groups or by one phenyl group which is disubstituted by $C_1$–$C_6$ alkoxy groups; or
(b) $R^4$ and $R^5$ form together with the nitrogen atom to which they are attached a heterocyclic group selected from groups of formulae (1) wherein $R^6$ and $R^7$ are both H or both $C_1$–$C_6$ alkoxy, or wherein $R^6$ and $R^7$ together form a methylenedioxy group; (2) wherein Y is O or —$NR^8$ wherein $R^8$ is methyl, phenyl or trifluoromethylphenyl; (3); and (4).

Preferably $R^4$ is methyl and $R^5$ is diphenylmethyl or 2-(3,4-dimethoxyphenyl)ethyl, or $R^4$ and $R^5$ together form instead heterocyclic ring (1) in which $R^6$ and $R^7$ are both H or both OMe, or together form a methylenedioxy group.

Examples of preferred compounds of formula (I) are as follows:

1-(4-((3Z,6Z)-6-Benzylidene-1-methyl-2,5-dioxo-3-piperazinylidene)methylbenzoyl)-4-(2-pyrimidyl) piperazine (9022);

1-(4-((3Z,6Z)-6-Benzylidene-1-methyl-2,5-dioxo-3-piperazinylidene)methylbenzoyl)-4-methylpiperazine, hydrochloride (9052);

1-(4-((3Z,6Z)-6-Benzylidene-1-methyl-2,5-dioxo-3-piperazinylidene)methylbenzoyl)-4-(4-methoxyphenyl) piperazine, hydrochloride (9071);

N-Allyl-4-((3Z,6Z)-6-benzylidene-1-methyl-2,5-dioxo-3-piperazinylidene)methylbenzamide (9070);

N-(2-Diphenylmethylmethylaminoethyl)-4-((3Z,6Z)-6-benzylidene-1-methyl-2,5-dioxo-3-piperazinylidene) methylbenzamide, hydrochloride (9076);

N-(2-(1,2,3,4-Tetrahydro-2-isoquinolyl)ethyl)-4-((3Z,6Z)-6-benzylidene-1-methyl-2,5-dioxo-3-piperazinylidene) methylbenzamide, hydrochloride (9116);

N-(3,4-Dimethoxyphenethyl)-4-((3Z,6Z)-6-benzylidene-1-methyl-2,5-dioxo-3-piperazinylidene)methylbenzamide (9117);

N-(4-(4-Phenyl-1-piperazinyl)methylphenyl)-4-((3Z,6Z)-6-benzylidene-1-methyl-2,5-dioxo-3-piperazinylidene) methylbenzamide, hydrochloride (9104);

N-(2-(4-Methyl-1-piperazinyl)ethyl)-4-((3Z,6Z)-6-benzylidene-1-methyl-2,5-dioxo-3-piperazinylidene) methylbenzamide (9007);

N-(2-Morpholinoethyl)-4-((3Z,6Z)-6-benzylidene-1-methyl-2,5-dioxo-3-piperazinylidene)methylbenzamide, hydrochloride (9053);

N-(4-Morpholinophenyl)-4-((3Z,6Z)-6-benzylidene-1-methyl-2,5-dioxo-3-piperazinylidene)methylbenzamide, hydrochloride (9054);

N-(4-(2-(1,2,3,4-Tetrahydro-β-carbolin-2-yl)ethyl)phenyl)-4-((3Z,6Z)-6-benzylidene-1-methyl-2,5-dioxo-3-piperazinylidene)methylbenzamide (9080);

N-(4-(1,2,3,4-Tetrahydro-β-carbolin-2-yl)methylphenyl)-4-((3Z,6Z)-6-benzylidene-1-methyl-2,5-dioxo-3-piperazinylidene)methylbenzamide (9096);

N-(4-(2-(4-Phenyl-1-piperazinyl)ethyl)phenyl)-4-((3Z,6Z)-6-benzylidene-1-methyl-2,5-dioxo-3-piperazinylidene)methylbenzamide (9103);

N-(4-(2-(1,2,3,4-Tetrahydro-2-isoquinolyl)ethyl)phenyl)-4-((3Z,6Z)-6-benzylidene-1-methyl-2,5-dioxo-3-piperazinylidene)methylbenzamide (9065);

N-(4-(2-(4-(3-Trifluoromethylphenyl)-1-piperazinyl)ethyl)phenyl)-4-((3Z,6Z)-6-benzylidene-1-methyl-2,5-dioxo-3-piperazinylidene)methylbenzamide (9049);

N-(4-(2-(4-(4-Chlorophenyl) -4-hydroxypiperidino)ethyl)phenyl)-4-((3Z,6Z)-6-benzylidene-1-methyl-2,5-dioxo-3-piperazinylidene)methylbenzamide (9079);

N-(4-(2-(6,7-Dimethoxy-1,2,3,4-tetrahydro-2-isoquinolyl)ethyl)phenyl)-4-((3Z,6Z)-6-benzylidene-1-methyl-2,5-dioxo-3-piperazinylidene)methylbenzamide (9006);

N-(2-(6,7-Dimethoxy-1,2,3,4-tetrahydro-2-isoquinolyl)ethyl)-4-((3Z,6Z)-6-benzylidene-1-methyl-2,5-dioxo-3-piperazinylidene)methylbenzamide (9008);

N-(4-(6,7-Dimethoxy-1,2,3,4-tetrahydro-2-isoquinolyl)methylphenyl)-4-((3Z,6Z)-6-benzylidene-1-methyl-2,5-dioxo-3-piperazinylidene)methylbenzamide, hydrochloride (9064);

(3Z,6Z)-6-Benzylidene-3-(4-(3-dimethylamino-2-hydroxypropoxy)benzylidene)-1-methyl-2,5-piperazinedione (9023);

(3Z,6Z)-6-Benzylidene-3-(4-(2-(6,7-dimethoxy-1,2,3,4-tetrahydro-2-isoquinolyl)ethyl)benzylidene)-1-methyl-2,5-piperazinedione (9115);

N-(4-(2-(6,7-Dimethoxy-1,2,3,4-tetrahydro-2-isoquinolyl)ethyl)phenyl)-3-((3Z,6Z)-6-benzylidene-1-methyl-2,5-dioxo-3-piperazinylidene)methylbenzamide, hydrochloride (9051);

N-(4-(6,7-Dimethoxy-1,2,3,4-tetrahydro-2-isoquinolyl)methylphenyl)-3-((3Z,6Z)-6-benzylidene-1-methyl-2,5-dioxo-3-piperazinylidene)methylbenzamide (9128);

N-(2-(6,7-Dimethoxy-1,2,3,4-tetrahydro-2-isoquinolyl)ethyl)- 3-((3Z,6Z)-6-benzylidene-1-methyl-2,5-dioxo-3-piperazinylidene)methylbenzamide (9136);

N-(2-(3,4-Dimethoxyphenethyl)methylamino)ethyl)-3-((3Z,6Z)-6-benzylidene-1-methyl-2,5-dioxo-3-piperazinylidene)methylbenzamide (9137);

N-(4-(2-(3,4-Dimethoxyphenethyl)methylamino)ethyl)phenyl)-3-((3Z,6Z)-6-benzylidene-1-methyl-2,5-dioxo-3-piperazinylidene)methylbenzamide (9138);

N-(4-(2-(4-Phenyl-1-piperazinyl)ethyl)phenyl)-3-((3Z,6Z)-6-benzylidene-1-methyl-2,5-dioxo-3-piperazinylidene)methylbenzamide (9083);

N-(4-(3-(6,7-Dimethoxy-1,2,3,4-tetrahydro-2-isoquinolyl)propyl)phenyl)-3-((3Z,6Z)-6-benzylidene-1-methyl-2,5-dioxo-3-piperazinylidene)methylbenzamide, hydrochloride (9161);

N-(2-(2,2-Diphenylethyl)methylaminoethyl)-3-((3Z,6Z)-6-benzylidene-1-methyl-2,5-dioxo-3-piperazinylidene)methylbenzamide (9163);

(3Z,6Z)-6-Benzylidene-3-(4-(4-(2-(6,7-dimethoxy-1,2,3,4-tetrahydro-2-isoquinolyl)ethyl)benzyloxy)benzylidene)-1-methyl-2,5-piperazinedione (9176);

(3Z,6Z)-6-Benzylidene-3-(3-(4-(2-(6,7-dimethoxy-1,2,3,4-tetrahydro-2-isoquinolyl)ethyl)benzyloxy)benzylidene)-1-methyl-2,5-piperazinedione (9177);

N-(4-((3Z,6Z)-6-Benzylidene-1-methyl-2,5-dioxo-3-piperazinylidene)methylphenyl)-4-(2-(6,7-dimethoxy-1,2,3,4-tetrahydro-2-isoquinolyl)ethyl)benzamide (9190);

1-(4-((3Z,6Z)-6-Benzylidene-1-methyl-2,5-dioxo-3-piperazinylidene)methylbenzoyl)-4-(6,7-dimethoxy-1,2,3,4-tetrahydroisoquinolyl)methylpiperidine (9200);

Compounds of formula (I) are produced by a process which comprises treating 1-acetyl-3-benzylidene-4-methyl-2,5-piperazinedione, which has the formula (II):

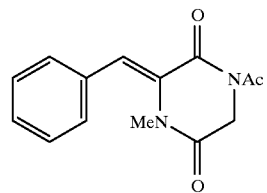

(II)

with an aldehyde of the following formula (III):

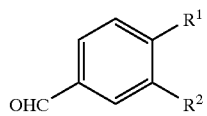

(III)

wherein $R^1$ and $R^2$ are as defined for formula (I), in an organic solvent in the presence of a base; and, if desired, converting the resulting compound into a pharmaceutically acceptable salt thereof.

Suitable bases include caesium carbonate, sodium carbonate, potassium carbonate, sodium hydride, potassium t-butoxide and triethylamine.

Suitable organic solvents include dimethylformamide (DMF), tetrahydrofuran (THF) and in the case of potassium t-butoxide, t-butanol and mixtures thereof.

When DMF is used as solvent the temperature is typically between 0° C. and reflux temperature, for example from 80° C. to 95° C. when caesium carbonate is used as base.

When sodium hydride or potassium t-butoxide is used as the base the reaction mixture is typically warmed from 0° C. to room temperature or to 40° C.

The duration of the reaction may be from 1 to 4 hours, for example from 2 to 3 hours.

The compound of formula (II) may be prepared as described in Reference Example 1 which follows. Compounds of formula (III) may be prepared from commercially available starting materials by conventional methods, the particular starting material and method employed depending upon the identity of the aldehyde. For instance, an aldehyde of formula (III) wherein one of $R^1$ and $R^2$ is hydrogen and the other is a group of formula —$COR^3$ as defined above may be prepared by a process which comprises treating a compound of formula (IV):

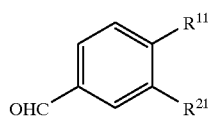

(IV)

wherein one or $R^{11}$ and $R^{21}$ is hydrogen and the other is —COOH, —COX wherein X is a halogen, or —CO(OCOR') wherein R' is $C_1$–$C_6$ alkyl, with an amine of formula

H—$R^3$ wherein $R^3$ is as defined above, in an inert organic solvent; the reaction being performed in the presence of a coupling agent when $R^{11}$ or $R^{21}$ is —COOH.

Suitable coupling agents for use when $R^{11}$ or $R^{12}$ is —COOH include 1,3-dicyclohexylcarbodiimide, 1-cyclohexyl-3-(2-morpholinoethyl)carbodiimide metho-p-toluenesulphonate and 2-chloro-1-methylpyridinium iodide.

When $R^{11}$ or $R^{21}$ is a group —COX or —CO(OCOR') as defined above, the reaction is optionally conducted in the presence of a base, for instance a tertiary amine such as $Et_3N$, or pyridine. The solvent is then suitably dichloromethane.

The activated compounds of formula (IV) wherein $R^{11}$ or $R^{21}$ is —COX or —CO(OCOR') may be prepared from the correspondingly compound of formula (IV) wherein $R^{11}$ or $R^{21}$, respectively, is the carboxy group —COOH by conventional methods which are routine in organic synthesis.

For instance, compounds wherein $R^{11}$ or $R^{21}$ is —COX may be prepared by treating the carboxy compound with a halogenating agent, for example a chlorinating agent such as $SOCl_2$, $PCl_3$, oxalyl chloride or $PCl_5$.

Compounds wherein $R^{11}$ or $R^{21}$ is —CO(OCOR') may be prepared by treating the carboxy compound with a $C_1$–$C_6$ alkyl haloformate in the presence of a tertiary amine, for instance EtOCOCl or iBuOCOCl in the presence of $Et_3N$. In this case it is generally convenient to treat the resulting mixture directly with the amine H—$R^3$.

When $R^3$ is a group of formula (A) as defined above in which n is 1 and v is 1, the amine H—$R^3$ may be prepared by reducing the corresponding nitro compound of formula (V):

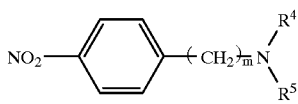

(V)

wherein m, $R^4$ and $R^5$ are as defined above for formula (A). The reduction may suitably be performed using iron powder and concentrated hydrochloric acid in methanol, typically under reflux. Alternatively, the reduction may be performed using hydrogen over a palladium on carbon catalyst.

A compound of formula (V) may be prepared by treating a compound of the following formula (VI):

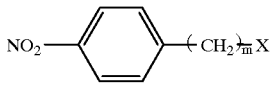

(VI)

wherein m is as defined in formula (V) and X is a halogen, with an amine of formula (VII):

(VII)

wherein $R^4$ and $R^5$ are as defined above for formula (A), in an organic solvent in the presence of base. The organic solvent is typically DMF or acetonitrile, and the base is typically $K_2CO_3$. The temperature is typically from room temperature to 100° C., for instance from 60° C. to 80° C. The duration of the reaction is usually from 1 to 30 hours, for instance 2 to 24 hours, typically from about 8 hours to about 12 hours.

When $R^3$ is a group of formula (A) as defined above in which n is 0 and v is 1, the amine H—$R^3$ may be prepared by reducing the corresponding nitrile of formula (VIII):

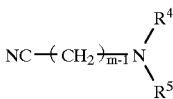

(VIII)

wherein m is 1, 2 or 3 and $R^4$ and $R^5$ are as defined above for formula (A). The reduction may suitably be performed with $LiAlH_4$ in ethylene glycol dimethyl ether, at a temperature between 0° C. and 40° C., typically warming from 0° C. to room temperature, for instance from 0° C. to 20° C. Other amines H—$R^3$ may be prepared by analogous methods using known starting materials, or are commercially available products.

A nitrile of formula (VIII) may be prepared by treating a compound of formula (VII) as defined above with a compound of formula (X):

(X)

wherein X is a halogen and m is as defined for formula (VIII), in an organic solvent in the presence of a base. The solvent is suitably acetonitrile. The base may be, for example, $K_2CO_3$. The reaction is typically carried out at the reflux temperature of the solvent for a period of from 1 hour to 30 hours, for instance from 1 hour to 20 hours.

An aldehyde of formula (III) wherein $R^1$ is a group of formula (D) may be prepared by treating the compound of formula (XI):

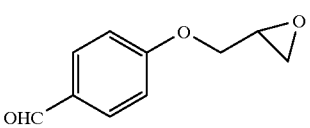

(XI)

with an amine of formula H—$N(R^{10})$ $(R^{11})$ wherein $R^{10}$ and $R^{11}$ are as defined for formula (D), in a suitable solvent. Such solvents include aqueous THF. The compound of formula (XI) may in turn be prepared by treatment of 4-hydroxybenzaldehyde with 1.5M sodium hydroxide followed by epichlorohydrin. This reaction is typically performed at about 50° C. for about 5 hours.

The aldehyde of formula (III) wherein $R^1$ is a group of formula (E) in which r is 2 (compound 5.1) may be prepared as described in Reference Example 5 which follows. Corresponding aldehydes in which r in formula (E) is 1 or 3 may be prepared by an analogous process, replacing the 4-(2-bromoethyl)benzoic acid used as starting material by 4-bromomethylbenzoic acid or 4-(3-bromopropyl)benzoic acid, respectively.

An aldehyde of formula (III) may also be prepared by treating the corresponding nitrile of formula (XII)

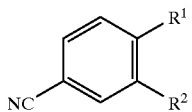
(XII)

with formic acid and Raney nickel, for instance as described in Reference Example 7 which follows.

Compounds of formula (I) may be converted into pharmaceutically acceptable salts, and salts may be converted into the free compound, by conventional methods. Suitable salts include salts with pharmaceutically acceptable inorganic or organic acids. Examples of inorganic acids include hydrochloric acid, sulphuric acid and orthophosphoric acid. Examples of organic acids include p-toluenesulphonic acid, methanesulphonic acid, mucic acid and succinic acid.

Cancer cells which exhibit multi-drug resistance, referred to as MDR cells, display a reduction in intracellular drug accumulation compared with the corresponding drug-sensitive cells. Studies using in vitro derived MDR cell lines have shown that MDR is often associated with increased expression of a plasma membrane glycoprotein (P-gp) which has drug binding properties. P-gp is thought to function as an efflux pump for many hydrophobic compounds, and transfection studies using cloned P-gp have shown that its overexpression can confer the MDR phenotype on cells: see, for example, Ann. Rev. Biochem 58 137–171 (1989).

A major function of P-gp in normal tissues is to export intracellular toxins from the cell. There is evidence to suggest that overexpression of P-gp may play a clinical role in multi-drug resistance. Increased levels of P-gp mRNA or protein have been detected in many forms of human cancers—leukaemias, lymphomas, sarcomas and carcinomas. Indeed, in some cases P-gp levels have been found to be increased in tumour biopsies obtained after relapse from chemotherapy.

Inhibition of P-gp function in P-gp mediated MDR has been shown to lead to a net accumulation of anti-cancer agent in the cells. For example, Verapamil a known calcium channel blocker was shown to sensitise MDR cells to Vinca alkaloids in vitro and in vivo: *Cancer Res.*, 41, 1967–1972 (1981). The proposed mechanism of action involves competition with the anti-cancer agent for binding to the P-gp. A range of structurally unrelated resistance-modifying agents acting by this mechanism have been described such as tamoxifen (Nolvadex:ICI) and related compounds, and cyclosporin A and derivatives.

Compounds of formula I and their pharmaceutically acceptable salts (hereinafter referred to as "the present compounds") have been found in biological tests to have activity in modulating multi-drug resistance. The results are set out in Example 3 which follows. The present compounds may therefore be used as multi-drug resistance modifying agents, also termed resistance-modifying agents, or RMAS. The present compounds can modulate, e.g. reduce, or eliminate multi-drug resistance.

The present compounds can therefore be used in a method of potentiating the cytotoxicity of an agent which is cytotoxic to a tumour cell. Such a method comprises, for instance, administering one of the present compounds to the tumour cell whilst the tumour cell is exposed to the cytotoxic agent in question. The therapeutic effect of a chemotherapeutic, or antineoplastic, agent may thus be enhanced. The multi-drug resistance of a tumour cell to a cytotoxic agent during chemotherapy may be reduced or eliminated.

The present compounds can also be used in a method of treating a disease in which the pathogen concerned exhibits multi-drug resistance, for instance multi-drug resistant forms of malaria (*Plasmodium falciparum*), tuberculosis, leishmaniasis and amoebic dysentery. Such a method comprises, for instance, administering one of the present compounds with (separately, simultaneously or sequentially) the drug to which the pathogen concerned exhibits multi-drug resistance. The therapeutic effect of the drug may thus be enhanced.

A human or animal patient harbouring a tumour may be treated for resistance to a chemotherapeutic agent by a method comprising the administration thereto of one of the present compounds. The present compound is administered in an amount effective to potentiate the cytotoxicity of the said chemotherapeutic agent. Examples of chemotherapeutic or antineoplastic agents which are preferred in the context of the present invention include Vinca alkaloids such as vincristine and vinblastine; anthracycline antibiotics such as daunorubicin and doxorubicin; mitoxantrone; actinomycin D; taxanes e.g. taxol; epipodophyllotoxins e.g. etoposide and plicamycin.

In addition, a human or animal patient suffering from a disease in which the responsible pathogen exhibits multi-drug resistance may be treated for resistance to a therapeutic agent by a method comprising the administration thereto of one of the present compounds.

Examples of such disease include multi-drug resistant forms of malaria (*Plasmodium falciiparum*), tuberculosis, leishmaniasis and amoebic dysentery.

MDR modulators also have utility in the delivery of drugs across the blood-brain barrier, and in the treatment of AIDS and AIDS-related complex. The present compounds car therefore be used in a method of facilitating the delivery of drugs across the blood brain barrier, and in the treatment of AIDS or AIDS-related complex. A human or animal patient in need of such treatment may be treated by a method comprising the administration thereto of one of the present compounds.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 50 mg/kg, most commonly in the range of 0.01 to 5 mg/kg, body weight. Such a dosage may be given, for example, from 1 to 5 times daily by bolus infusion, infusion over several hours and/or repeated administration.

A piperazinedione derivative of formula (I) or a pharmaceutically acceptable salt thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as a modulator of multi-drug resistance comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. Such compounds may be encapsulated within liposomes.

The invention will be further illustrated in the Examples which follow.

REFERENCE EXAMPLE 1

1-acetyl-3-benzylidene-4-methyl-2,5-piperazinedione 1,4-Diacetyl-2,5-piperazinedione (described by Marcuccio and Elix in Aust. J. Chem, 1984, 37, 1791) (25.0 g, 126 mmol) was treated at 130° C. in DMF (200 ml) with triethylamine (17.6 ml, 126 mmol) and benzaldehyde (13.0 ml, 126 mmol). After 4 hours the mixture was cooled to room temperature and poured into EtOAc (1000 ml) and washed 3 times with brine. Any solid formed at this stage was filtered off. The filtrate was dried (MgSO$_4$) and the solvent removed in vacuo. The residue was recrystallised from EtOAc:Hexane to give 11.78 g (38%) of 1-acetyl-3-benzylidene-2,5-piperazinedione.

The latter compound was treated with NaH and MeI in DMF: THF (1:5) at a temperature of 0° C. and allowed to warm to room temperature to give the title compound in 57% yield.

REFERENCE EXAMPLE 2

Preparation of Amines H—R$^3$ via Substituted Nitrobenzene

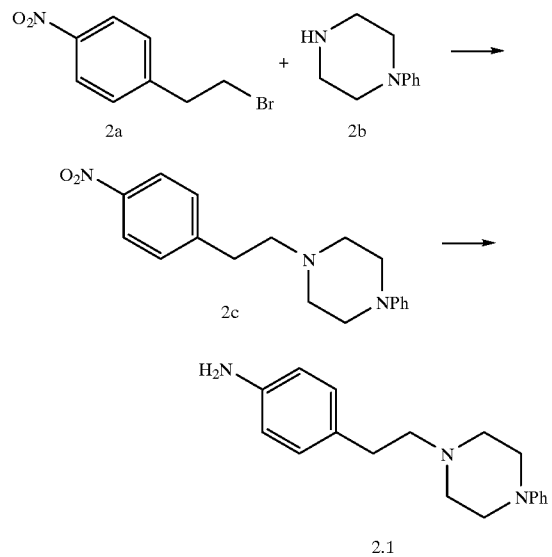

4-Bromoethyl nitrobenzene (2a) was treated with 1-phenylpiperazine (2b) in the presence of K$_2$CO$_3$ in DMF at 80° C. for 8 hours. Compound 2c was obtained in 58% yield. 2c was then reduced by treatment with iron powder and concentrated HCl in MeOH under reflux for 3 hours. The desired amine 2.1 was obtained in 40% yield.

Following an analogous synthetic route, but using where necessary 4-bromomethylnitrobenzene or 4-(3-bromopropyl)nitrobenzene in place of 4-(2-bromoethyl) nitrobenzene (2a), and replacing 4-phenylpiperazine (2b) by the appropriate compound of formula (VII), further amines H—R$^3$ were prepared as shown in Table 1. The conditions employed at each stage in the preparation of these further amines were as described above for amine 2.1, except for amine 2.9 where the reduction step was conducted using hydrogen at 50 p.s.i. over palladium on carbon, in ethanol. This reduction was performed for 2.5 hours at room temperature. In the case of amine 2.4, reduction of the nitro group was accompanied by hydrogenolysis of the 4-chlorophenyl group to give the amine 2.4.

TABLE 1
| Compound (VI) | Compound VII | Amine H—R³ (N°) |
|---|---|---|
| 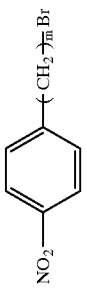 wherein m is: | | |
| 2 | 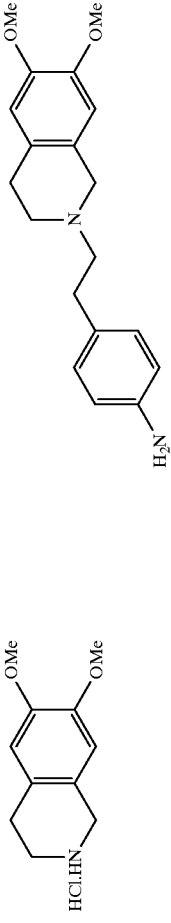 | 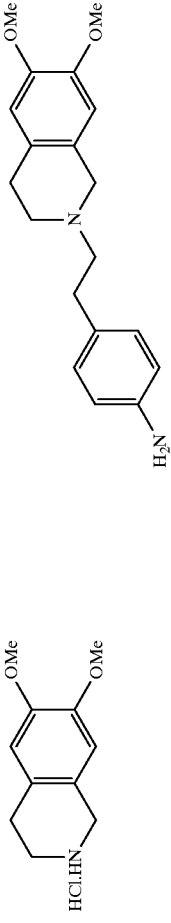 (2.1) |
| 2 | 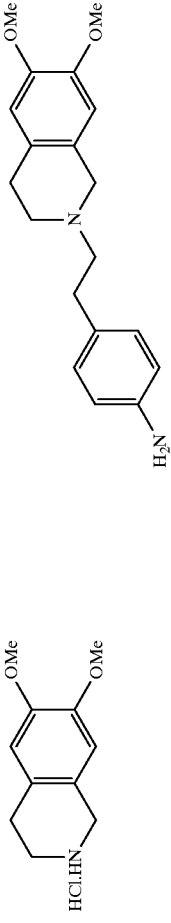 | 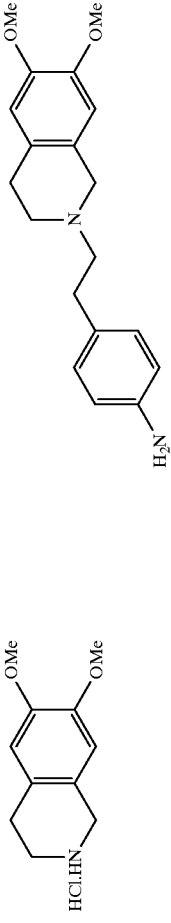 (2.2) |
| 2 | 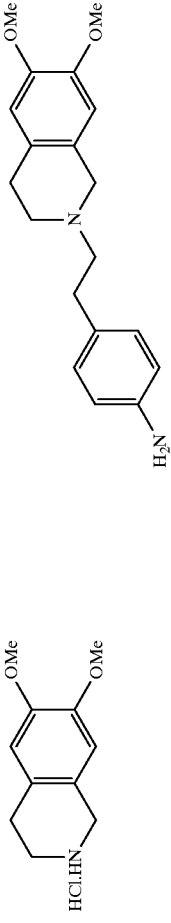 | 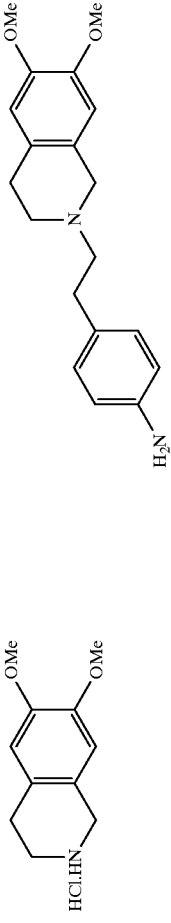 (2.3) |
| 2 | 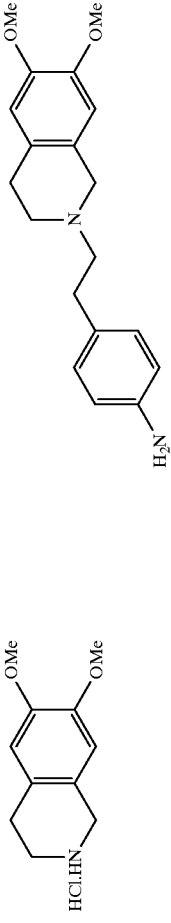 | 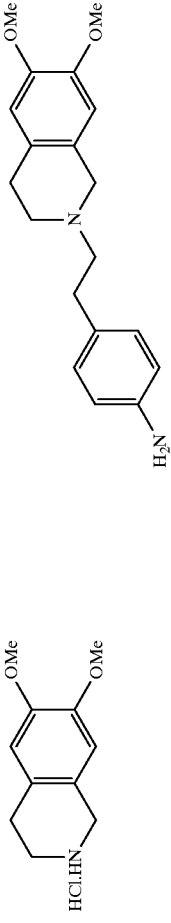 (2.4) |
| | | 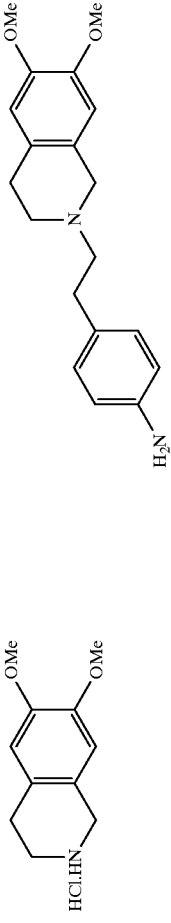 (2.5) |

TABLE 1-continued

| Compound (VI) | Compound VII | Amine H—R³ (N°) |
|---|---|---|
| 4-NO₂-C₆H₄-(CH₂)ₘ-Br, wherein m is: | | |
| 1 | piperazine-NPh (HN-piperazine-NPh) | 4-H₂N-C₆H₄-CH₂-piperazine-NPh (2.6) |
| 1 | 6,7-dimethoxy-1,2,3,4-tetrahydroisoquinoline·HCl | 4-H₂N-C₆H₄-CH₂-(6,7-dimethoxy-tetrahydroisoquinolin-2-yl) (2.7) |
| 1 | 2,3,4,9-tetrahydro-1H-β-carboline (HN) | 4-H₂N-C₆H₄-CH₂-(2,3,4,9-tetrahydro-β-carbolin-2-yl) (2.8) |
| 2 | 3,4-dimethoxy-N-methylphenethylamine (MeNH) | 4-H₂N-C₆H₄-(CH₂)₂-N(Me)-CH₂CH₂-(3,4-dimethoxyphenyl) (2.9) |
| 3 | 6,7-dimethoxy-1,2,3,4-tetrahydroisoquinoline·HCl | 4-H₂N-C₆H₄-(CH₂)₃-(6,7-dimethoxy-tetrahydroisoquinolin-2-yl) (2.10) |

REFERENCE EXAMPLE 3

Preparation of Amines H—R³ via Substituted Nitrile

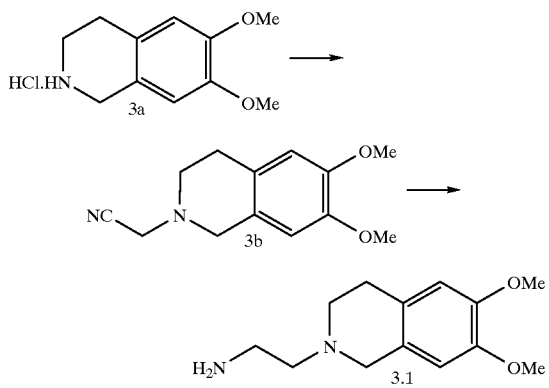

6,7-Dimethoxy-1,2,3,4-tetrahydroisoquinoline hydrochloride (3a) was treated with chloroacetonitrile in the presence of $K_2CO_3$ in acetonitrile under reflux for 24 hours. Compound 3b was obtained in 92% yield. 3b was then treated with $LiAlH_4$ in ethylene glycol dimethyl ether at room temperature overnight. The temperature was then raised to 40° C. and the reaction continued for 30 minutes. The desired amine 3.1 was obtained in 98% yield.

Following an analogous synthetic route, but modifying the conditions of the first step where necessary and replacing compound 3a by the appropriate compound of formula VII, the further amines H—R³ listed in Table 2 were prepared:

TABLE 2

| Compound of formula VII | Conditions of first step | Amine H—R³ (No) |
|---|---|---|
| [HN piperazine NMe] | $K_2CO_3$, $ClCH_2CN$, $CH_3CN$ reflux 20 h | [H₂N-CH₂CH₂-N piperazine NMe] (3.2) |
| [H—N(Me)(CHPh₂)] | $K_2CO_3$ $ClCH_2CN$, $CH_3CN$ reflux, 24 h | [H₂N-CH₂CH₂-N(Me)(CHPh₂)] (3.3) |
| [HN tetrahydroisoquinoline] | $K_2CO_3$ $ClCH_2CN$, $CH_3CN$ reflux 24 h | [H₂N-CH₂CH₂-N tetrahydroisoquinoline] (3.4) |
| [HCl.HN 6,7-dimethoxy-tetrahydroisoquinoline] | $K_2CO_3$ $ClCH_2CN$, $CH_3CN$ reflux 24 h | [H₂N-CH₂CH₂-N 6,7-dimethoxy-tetrahydroisoquinoline] (3.5) |
| [MeNH-CH₂CH₂-3,4-dimethoxyphenyl] | $K_2CO_3$, $ClCH_2CN$ $CH_3CN$ reflux 4 h | [H₂N-CH₂CH₂-N(Me)-CH₂CH₂-3,4-dimethoxyphenyl] (3.6) |

REFERENCE EXAMPLE 4

Preparation of Further Amines H—R³

1. (3,4-Dimethoxyphenethyl)Methylamine

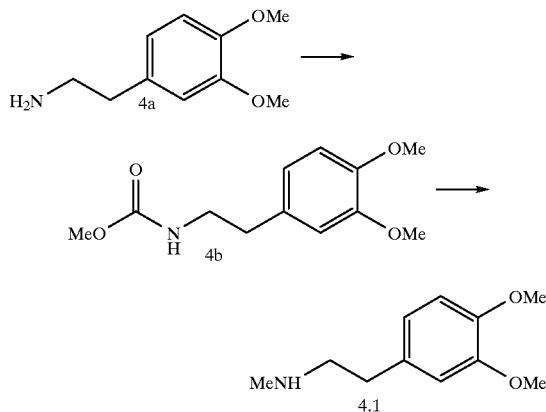

2-(3,4-Dimethoxyphenyl)ethylamine (4a) was treated with MeOCOl in the presence of triethylamine in CH₂Cl₂ at −78° C. and allowed to warm to 0° C. overnight. Compound 4b was obtained in 9% yield. 4b was treated with LiAlH₄ in THF at a temperature of 0° C. and allowed to warm to room temperature overnight. Compound 4.1, which is the starting amine used to prepare compound 2.9 in Reference Example 2, was obtained in 91% yield.

2. H₂N—(CH₂)₂—NMe—CH₂CHPh₂

2,2-Diphenylethylamine was treated with (CF₃CO)₂O in Et₂O at 0° C. for 1 hour. The resulting compound (Ph)₂—CH—CH₂—NHCOCF₃, obtained in quantitative yield, was treated with KH in THF at 0° C. followed by MeI and 18-crown-6 at room temperature for 24 hours to give (Ph)₂—CH—CH₂—NMeCOCF₃ in 91% yield. The latter compound was treated with 2M NaOH in methanol under reflux for 2 hours to give (Ph)₂—CH—CH₂NHMe in 81% yield, which in turn was treated with chloroacetonitrile in the presence of K₂CO₃ in acetonitrile under reflux for 24 hours to give (Ph)₂—CH—CH₂—NMe—CH₂CN in 83% yield. Reduction of this compound with LiAlH₄ in ethylene glycol dimethyl ether at room temperature for 2 hours gave the title amine, which is compound 4.2, in 90% yield.

3. Amine 4.3

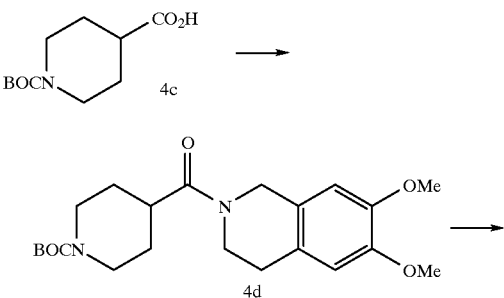

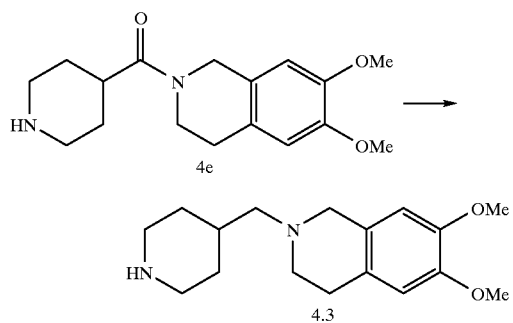

Compound 4c was treated with 6,7-dimethoxy-1,2,3,4-tetrahydroisoquinoline in CH₂Cl₂ at 0° C. in the presence of 2-chloro-1-methylpyridinium iodide and triethylamine. The solution was allowed to warm to room temperature overnight. Compound 4d, which was obtained in 93% yield, was treated with trifluoroacetic acid in dichloromethane at room temperature for 30 minutes. Compound 4e was obtained in 10% yield after trituration with acetone. Compound 4e was treated with LiAlH₄ in THF at 10° C. and left overnight to warm to room temperature. Compound 4.3 was obtained in 75% yield.

REFERENCE EXAMPLE 5

Preparation of Aldehyde 5.1

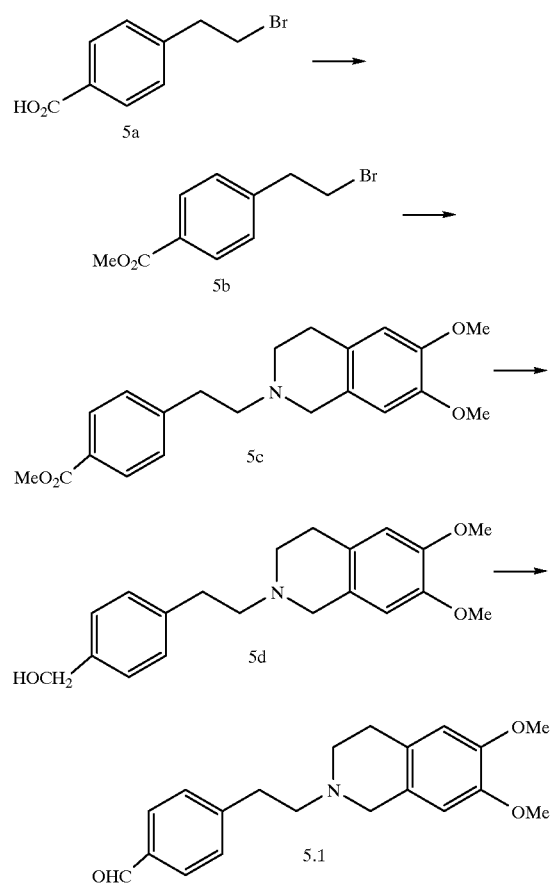

Compound 5a was treated with excess CH₂N₂ in THF at 0° C. for 7 hours. 5b was obtained in 98% yield. Compound 5b was then treated with 6,7-dimethoxy-1,2,3,4-tetrahydroisoquinoline hydrochloride in DMF in the presence of $K_2CO_3$ at room temperature for 5 days to give 5c in 56% yield. Compound 5c was reduced by treatment with $LiAlH_4$ in THF at room temperature for 1 hour to give 5d (80% yield), which in turn was treated with pyridinium chlorochromate (PCC) buffered with NaOAc in $CH_2Cl_2$ at room temperature for 16 hours. Compound 5.1 was obtained in 25% yield.

REFERENCE EXAMPLE 6

Preparation of Aldehydes of Formula (III)

Method 1

The aldehydes of formula IIIa listed in Table 3 below were prepared by treating 3-formylbenzoic acid with the appropriate amine $H—R^3$ (a compound prepared in one of Reference Examples 2 and 3) in $CH_2Cl_2$ in the presence of 2-chloro-1-methylpyridinium iodide at 0° C. The reaction was allowed to warm to room temperature overnight.

TABLE 3

Aldehydes of formula IIIa (IIIa)

| Aldehyde No. | $R^3$ | Corresponding amine $H—R^3$ |
|---|---|---|
| 6.1 | (4-aminophenethyl)-6,7-dimethoxy-tetrahydroisoquinoline | 2.2 |
| 6.2 | (4-aminophenethyl)-4-phenylpiperazine | 2.1 |
| 6.3 | (4-aminobenzyl)-6,7-dimethoxy-tetrahydroisoquinoline | 2.7 |
| 6.4 | N-(4-aminophenethyl)-N-methyl-N-(3,4-dimethoxyphenethyl)amine | 2.9 |
| 6.5 | (2-aminoethyl)-6,7-dimethoxy-tetrahydroisoquinoline | 3.5 |
| 6.6 | N-(2-aminoethyl)-N-methyl-N-(3,4-dimethoxyphenethyl)amine | 3.6 |
| 6.29 | N-(2-aminoethyl)-N-methyl-N-(2,2-diphenylethyl)amine | 4.2 |

Method 2

The aldehydes of formula IIIb listed in Table 4 below were prepared by treating 4-formylbenzoyl chloride with the appropriate amine H—R³ in CH₂Cl₂ in the presence of triethylamine at 0° C. In the case of aldehyde 6.32, 4-carboxybenzaldehyde was used in place of 4-formylbenzoyl chloride and 2-chloro-1-pyridinium iodide was additionally present in the reaction mixture. The reaction was allowed to warm to room temperature overnight. Each amine was either a compound prepared in one of Reference Examples 2 and 3, or a commercially available product.

TABLE 4

Aldehydes of formula IIIb (IIIb)

| Aldehyde No. | R³ | Corresponding amine H—R³ |
|---|---|---|
| 6.7 | (4-NH-phenyl-ethyl-N-(6,7-dimethoxy-tetrahydroisoquinoline)) | 2.2 |
| 6.8 | —NH-ethyl-N-(4-methylpiperazine) | 3.2 |
| 6.9 | —NH-ethyl-N-(6,7-dimethoxy-tetrahydroisoquinoline) | 3.1 |
| 6.10 | N-piperazinyl-pyrimidine | Commercial product |
| 6.11 | —NH-(4-phenyl-ethyl)-N-piperazinyl-N'-(3-trifluoromethylphenyl) | Commercial product |
| 6.12 | —N-(4-methylpiperazine) | Commercial product |
| 6.13 | —NH-ethyl-morpholine | Commercial product |
| 6.14 | —NH-(4-phenyl)-morpholine | Commercial product |

TABLE 4-continued

Aldehydes of formula IIIb (IIIb)

OHC—⟨C₆H₄⟩—COR³

| Aldehyde No. | R³ | Corresponding amine H—R³ |
|---|---|---|
| 6.15 | —NH—⟨C₆H₄⟩—CH₂—N(tetrahydroisoquinoline-6,7-diOMe) | 2.7 |
| 6.16 | —NH—⟨C₆H₄⟩—CH₂CH₂—N(tetrahydroisoquinoline) | 2.3 |
| 6.17 | —NH—CH₂CH=CH₂ | Commercial product |
| 6.18 | —N(piperazine)-N'-⟨C₆H₄⟩—OMe | Commercial product |
| 6.19 | —NH—CH₂CH₂—N(Me)—CHPh₂ | 3.3 |
| 6.20 | —NH—⟨C₆H₄⟩—CH₂CH₂—N(4-hydroxy-4-phenylpiperidine) | 2.4 |
| 6.21 | —NH—⟨C₆H₄⟩—CH₂CH₂—N(tetrahydro-β-carboline) | 2.5 |
| 6.22 | —NH—⟨C₆H₄⟩—CH₂—N(tetrahydro-β-carboline) | 2.8 |
| 6.23 | —NH—⟨C₆H₄⟩—CH₂CH₂—N(piperazine)-N'-Ph | 2.1 |

TABLE 4-continued

Aldehydes of formula IIIb

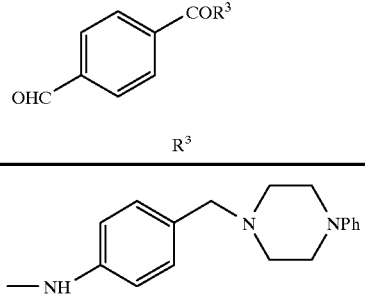
(IIIb)

| Aldehyde No. | R³ | Corresponding amine H—R³ |
|---|---|---|
| 6.24 | 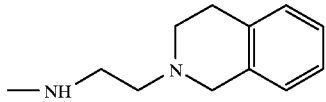 | 2.6 |
| 6.25 | | 3.4 |
| 6.26 | | Commercial product |
| 6.27 | | 2.10 |
| 6.32 | | 4.3 |

Method 3

By treating the compound of formula (XI) defined above in THF with aqueous HNMe₂ at room temperature for about 2 hours, the following aldehyde of formula (III) was produced in 91% yield:

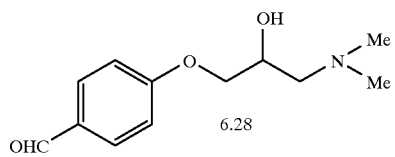
6.28

Method 4

Compound 5d, described in Reference Example 5, was treated with 4-hydroxybenzaldehyde in THF at 0° C. in the presence of triphenylphosphine and diethyl azidocarboxylate to give the following aldehyde of formula (III) in 40% yield:

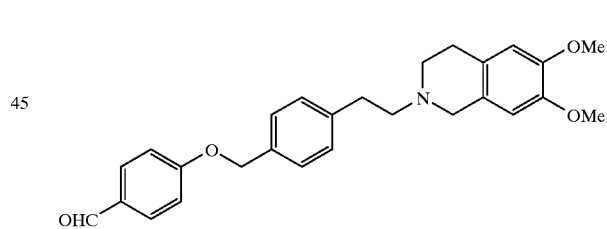

The above process was repeated, but using 3-hyaroxybenzaldehyde in place of 4-hydroxybenzaldehyde. The following aldehyde of formula (III) was produced in 50% yield:

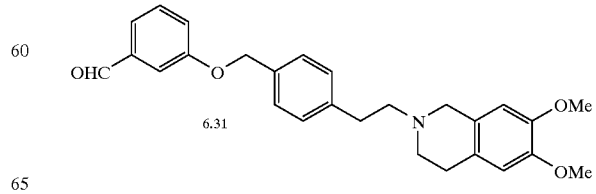
6.31

REFERENCE EXAMPLE 7

Preparation of Aldehyde 7.1

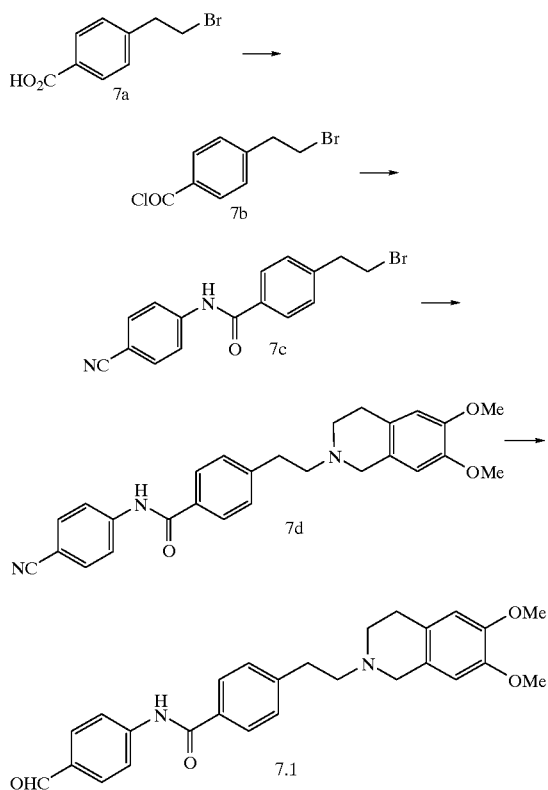

7a was treated with an excess of SOCl$_2$ and a catalytic amount of DMF in toluene under reflux for 4 hours. The resulting compound 7b was treated with 4-aminobenzonitrile in CH$_2$Cl$_2$ in the presence of triethylamine at 0° C. The reaction mixture was warmed to room temperature overnight. Flash chromatography (1:1 hexane-:ethyl acetate) gave 7c in 39% yield, which was treated with 6,7-dimethoxy-1,2,3,4-tetrahydroisoquinoline in the presence of K$_2$CO$_3$ in acetonitrile under reflux for 18 hours. Flash chromatography (10% methanol in ethyl acetate) gave 7d in 25% yield. 7d was treated with formic acid and a 50% slurry in water of Raney nickel under reflux for 2 hours. The aldehyde 7.1 was obtained in 71% yield.

EXAMPLE 1

Preparation of compounds of formula (I)

By treating 1-acetyl-3-benzylidene-4-methyl-2,5-piperazinedione, as described in Reference Example 1, with an aldehyde prepared in one of Reference Examples 5, 6 or 7 in DMF in the presence of Cs$_2$CO$_3$, at a temperature of between 80 and 90° C., the compounds of formula I listed in Table 5 were prepared:

TABLE 5

| Aldehyde N° | Compound of formula I |
|---|---|
| 6.7 | 9006 |
| 6.8 | 9007 |
| 6.9 | 9008 |

TABLE 5-continued

| Aldehyde N° | Compound of formula I |
|---|---|
| 6.10 | 9022 |
| 6.28 | 9023 |
| 6.11 | 9049 |
| 6.1 | 9051 |
| 6.12 | 9052 |
| 6.13 | 9053 |
| 6.14 | 9054 |
| 6.15 | 9064 |
| 6.16 | 9065 |
| 6.17 | 9070 |
| 6.18 | 9071 |
| 6.19 | 9076 |
| 6.20 | 9079 |
| 6.21 | 9080 |
| 6.2 | 9083 |
| 6.22 | 9096 |
| 6.23 | 9103 |
| 6.24 | 9104 |
| 5.1 | 9115 |
| 6.25 | 9116 |
| 6.26 | 9117 |
| 6.3 | 9128 |
| 6.5 | 9136 |
| 6.6 | 9137 |
| 6.4 | 9138 |
| 6.27 | 9161 |
| 6.29 | 9163 |
| 6.30 | 9176 |
| 6.31 | 9177 |
| 7.1 | 9190 |
| 6.32 | 9200 |

Compounds 9052, 9071, 9076, 9116, 9104, 9053, 9054, 9064 and 9051 were converted in a final step to their hydrochloride salts, by bubbling gaseous HCl through a solution of each compound in THF. (For these compounds the hydrochloride salt rather than the free base was used in the biological testing described in Example 3).

EXAMPLE 2

Pharmaceutical Composition

Tablets, each weighing 0.15 g and containing 25 mg of a compound of the invention can be manufactured as follows:
Composition for 10,000 tablets
compound of the invention (250 g)
lactose (800 g)
corn starch (415 g)
talc powder (30 g)
magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 3

Testing of Compounds (I) as Modulators of MDR
Materials and Methods

The EMT6 mouse mammary carcinoma cell line and the MDR resistant sublime AR 1.0 were cultured in RPMI 1640 medium containing 10% foetal calf serum and 2 mM glutamine at 37° C. in 5% CO$_2$. Cells were passaged between 1 in 200 and 1 in 2000 in the case of the parental cell line and between 1 in 20 and 1 in 200 in the case of the MDR resistant subline, after trypsinisation (0.25% trypsin, 0.2 gl$^{-1}$, EDTA).

1. Drug Accumulation Assay

AR 1.0 cells were seeded into 96 well opaque culture plates (Canberra Packard). The assay medium contained a mixture of tritiated Daunorubicin (DNR), a cytotoxic agent, and unlabelled DNR (0.3 μCi/ml; 2 μM). Compounds of formula I were serially diluted in assay medium over a range of concentrations from 5 nM to 100 μM. The cells were incubated at 37° C. for 1 hr before washing and determination of cell associated radioactivity. Results were expressed as % maximum accumulation where 100% accumulation is that observed in the presence of the known RMA verapamil at 100 μM. Where possible an IC$_{50}$ was determined.

The results are set out in the following Table 6.

TABLE 6

| Compound No. | IC$_{50}$ (μM) Accumulation | Max Accumulation |
|---|---|---|
| 9006 | 0.4 | |
| 9007 | | 30% |
| 9008 | 3.0 | |
| 9022 | 7.0 | |
| 9023 | | 30% |
| 9049 | | 20% |
| 9051 | 0.15 | |
| 9052 | 100 | |
| 9053 | 50 | |
| 9054 | | 32% |
| 9064 | 0.3 | |
| 9065 | 6 | |
| 9070 | 5 | |
| 9071 | 6 | |
| 9076 | | 44% |
| 9079 | 80 | |
| 9080 | | 18% |
| 9083 | 2 | |
| 9096 | | 20% |
| 9103 | | 20% |
| 9104 | 5 | |
| 9115 | 5 | |
| 9116 | 4 | |
| 9117 | 5 | |
| 9128 | 3 | |
| 9136 | 0.9 | |
| 9137 | 2 | |
| 9138 | 0.8 | |
| 9161 | | 20% |
| 9163 | 2.0 | |
| 9176 | 1.000 | |
| 9177 | 1.750 | |
| 9190 | 0.350 | |
| 9200 | 1.700 | |

2. Potention of Doxorubicin Toxicity

Compounds of formula (I) were examined for their ability to potentiate the toxicity of doxorubicin in AR 1.0 cells. In initial proliferation assays compounds were titrated against a fixed concentration of doxorubicin (0.86 μm) which alone is non-toxic to AR 1.0 cells. After a four day incubation with doxorubicin proliferation was measured using the colorimetric sulphorhodamine B assay (Skehan et al; J.Natl. Cancer Inst. 82 pp 1107–1112 (1990)). The results are shown in Table 7.

Compounds which were shown to be able to sensitise AR 1.0 cells to 0.86 μM doxorubicin without high innate selected for further study. Cells were cultured for four days with a titration of doxorubicin (0.01 nm–50 μM) in the presence of a fixed concentration of each compound. Proliferation was quantified as described by Skehan et. al, loc cit. The IC$_{50}$ (concentration required to reduce proliferation to 50% of the untreated controls) for doxorubicin alone and with each compound were derived and used to calculate the potentiation index (PI):

$$PI = \frac{IC_{50} \text{ for Doxorubicin alone}}{IC_{50} \text{ for Doxorubicin plus RMA}}$$

The results are shown in Table 8:

TABLE 7

| Compound No. | Compound toxicity (IC$_{50}$ μM) | Toxicity with cytotoxic agent (IC$_{50}$ μM) |
|---|---|---|
| 9006 | 2 | 0.04 |
| 9008 | 10 | 2.0 |
| 9022 | 35 | 0.8 |
| 9023 | 10 | 5.0 |
| 9049 | 2 | 0.2 |
| 9051 | 2 | 0.01 |
| 9053 | 40 | 4.0 |
| 9054 | 50 | 30 |
| 9064 | 2 | 0.01 |
| 9065 | 2 | 0.2 |
| 9070 | 40 | 4.0 |
| 9071 | 6 | 0.2 |
| 9079 | 2 | 1.7 |
| 9083 | 3 | 0.1 |
| 9104 | 40 | 0.05 |
| 9115 | 60 | 2.0 |
| 9116 | 8 | 1 |
| 9117 | 8 | 3 |
| 9128 | 10 | 2 |
| 9136 | 13 | 2 |
| 9137 | 12 | 4.5 |
| 9138 | 8 | 1.0 |
| 9163 | 10 | 0.5 |
| 9176 | 10 | 0.2 |
| 9177 | 15 | 0.5 |
| 9190 | 15 | 0.05 |
| 9200 | 13 | 0.8 |

TABLE 8

Potentiation Indices

| Compound No. | Potentiation index (RMA at 1 μM) |
|---|---|
| 9006 | 1000 |
| 9022 | 5 |
| 9049 | 15 |
| 9051 | 2000 |
| 9064 | 750 |
| 9065 | 15 |
| 9071 | 4 |
| 9079 | 3 |
| 9104 | 17 |
| 9136 | 25 |
| 9138 | 333 |
| 9163 | 6.7 |
| 9176 | 300.0 |
| 9177 | 75.0 |
| 9190 | 75.0 (measured at 0.3 μM) |
| | 10.0 (measured at 0.1 μM) |
| | 3.3 (measured at 0.03 μM) |
| | 1.4 (measured at 0.01 μM) |

EXAMPLE 4

Characterisation of the Present Compounds

The compounds and salts prepared in the preceding Examples were characterised by mass spectroscopic, microanalytical and proton nmr techniques. The results are set out in Tables 9 and 10:

TABLE 9

| No. | Mol. Formula | Mass spec data | | | ¹H nmr data | | Microanalysis | | |
| | | mass (intensity) | mode | solvent/field | δ | | Calc | Found | |
|---|---|---|---|---|---|---|---|---|---|
| 9023 | $C_{24}H_{27}N_3O_4$ | 422(100) | ESI | CDCl$_3$/ 400 MHz | 2.35 (6H,s), 2.41 (1H,dd), 2.57 (1H,dd), 2.99 (3H,s), 4.02 (2H,m), 4.08 (1H,m), 7.00–7.03 (3H,m), 7.28 –7.42 (8H,m), 7.95 (1H,b) | C<br>H<br>N | 68.39<br>6.46<br>9.97 | 68.09<br>6.44<br>9.81 | 68.26<br>6.42<br>9.81 |
| 9052 | $C_{25}H_{26}N_4O_3$ HCl | 431(100), 331(50) | FAB+ | d$_6$-DMSO/ 300 MHz | 2.75 (3H,s), 2.88 (3H,s), 3.10–3.30 (4H,bs), 3.35 (4H,bs), 6.85 (1H,s), 7.12 (1H,s), 7.32–7.40 (5H,m), 7.48 (2H,d), 7.65 (2H,d), 10.30 (1H,bs) | C<br>H<br>N | 64.3<br>5.85<br>12.0 | 64.3<br>5.80<br>11.6 | |
| 9054 | $C_{30}H_{28}N_4O_4$ HCl | 509(40), 508(45), 331(35), 178(100) | CI | d$_6$-DMSO/ 300 MHz | 2.96 (3H,s) 3.40 (4H,bs), 3.99 (4H,bs), 6.98 (1H,s), 7.20 (1H,s), 7.43–7.56 (7H,m), 7.82 (2H,d), 7.89 (2H,d), 8.12 (2H,d) 10.43 (1H,s), 10.83 (1H,s) | C<br>H<br>N | 66.1<br>5.35<br>10.3 | 66.0<br>5.30<br>10.3 | |

TABLE 10

| No. | Mol. Formula | Mass spec data | | ¹H nmr data | |
| | | mass (intensity) | mode | solvent/field | δ |
|---|---|---|---|---|---|
| 9006 | $C_{39}H_{38}N_2O_5$ | 643(100) | ESI | d$_6$-DMSD/400 MHz | 2.87 (3H,s), 2.89–3.23 (8H,m), 3.73 (2x3H,s), 4.20–4.54 (2H,m), 6.78 (1H,s), 6.82 (1H,s), 6.88 (1H,s), 7.09 (1H,s), 7.20–8.07 (13H,m), 10.30 (1H,s), 10.62 (1H,s), 11.01 (1H,bs) |
| 9007 | $C_{27}H_{31}N_5O_3$ | 474(100) | ESI | CDCl$_3$/400 MHz | 2.35 (3H,s), 2.49–2.73 (10H,m), 3.02 (3H,s), 3.59 (2H,m), 7.07 (1H,s), 7.28–7.44 (6H,m), 7.50 (2H,d), 7.86 (2H,d) |
| 9008 | $C_{33}H_{34}N_4O_5$ | 567(100) | ESI | CDCl$_3$/400 MHz | 2.76–2.90 (6H,m), 3.02 (3H,s), 3.61–3.70 (4H,m), 3.85 (2x3H,s), 6.55 (1H.s), 6.64 (1H,s), 6.94 (1H,bs), 7.07 (1H.s), 7.27–7.43 (6H,m), 7.47 (2H,d), 7.85 (2H,d) |
| 9022 | $C_{28}H_{26}N_6O_3$ | 495(20), 331(100) | ESI | CDCl$_3$/400 MHz | 3.02 (3H,s), 3.35–4.07 (8H,m), 6.56 (1H,t), 7.08 (1H,s), 7.29–7.43 (6H,m), 7.50 (2H,d), 7.55 (2H,d) 8.83 (2H,d) |
| 9049 | $C_{39}H_{36}F_3N_5O_3$ | 680(100) | ESI | CDCl$_3$/400 MHz | 2.64–2.75 (6H,m), 2.87 (2H,m), 3.04 (3H,s), 3.23–3.31 (4H,m), 7.04–7.10 (3H,m), 7.12 (1H,s) 7.23–7.42 (9H,m), 7.55 (2H,d), 7.59 (2H,d), 7.78 (1H,s), 7.96 (2H,d) |
| 9051 | $C_{39}H_{38}N_4O_5 \cdot HCl$ | 643(22), 348(30), 206(100) | CI | d$_6$-DMSO/400 MHz | 2.86 (3H,s), 2.92–3.18 (6H m) 3.36–3.48 (2H,m), 3.73 (2x3H,s), 4.22–4.55 (2H,m), 6.78 (1H,s), 6.82 (1H,s), 6.89 (1H,s), 7.09 (1H,s), 7.28–8.14 (13H,m), 10.29 (1H,s), 10.69 (2H,bs) |
| 9053 | $C_{26}H_{28}N_4O_4 \cdot HCl$ | 461(100), 331(10), | FAB+ | d$_5$-DMSO/300 MHz | 2.82 (3H,s), 3.05–3.20 (2H,bs), 3.45–3.62 (2H,bs), 3.68–3.78 (4H,bs), 3.80–3.90 (2H,bs), 3.90–4.00 (2H,bs), 6.82 (1H,s), 7.07 (1H,s), 7.33–7.48 (5H,m), 7.66 (2H,d), 7.96 (2H,d), 8.80–9.05 (1H,bs), 10.15 (1H,s), 10.95–11.15 (1H,bs) |
| 9064 | $C_{38}H_{36}N_4O_5 \cdot HCl$ | 629(100) | ESI | d$_6$-DMSO/ 400 MHz | 2.87 (3H.s), 2.90–3.40 (4H,m), 3.70 (2x3H,s), 4.10–4.52 (4H,m), 6.80 (2x1H,s), 6.89 (1H,s), 7.11 (1H,s), 7.30–7.45 (5H,m), 7.59 (2H,d), 7.73 (2H,d), 7.91 (2H,d), 8.02 (2H,d), 10.46 (1H,s), 10.64 (2H,bs) |
| 9065 | $C_{37}H_{34}N_4O_3$ | 582(10), 449(30), 331(100) | CI | CDCl$_3$/400 MHz | 2.65–3.10 (11H,m), 3.74 (2H,s), 6.95–8.10 (21H,m) |

TABLE 10-continued

| | | Mass spec data | | ¹H nmr data | |
|---|---|---|---|---|---|
| No. | Mol. Formula | mass (intensity) | mode | solvent/field | δ |
| 9070 | C₂₃H₂₁N₃O₃ | 388(100) | CI | CDCl₃/300 MHz | 3.05 (3H,s), 4.15 (2H,t), 5.35 (2H,m), 5.95 (1H,m), 6.24 (1H,bs), 7.10 (1H,s), 7.32–7.46 (6H,m), 7.53 (2H,d), 7.90 (2H,d), 8.05 (1H,bs) |
| 9071 | C₃₁H₃₀N₄O₄·HCl | 523(100), 331(75), 162(60) | FAB+ | d₆-DMSO/300 MHz | 2.88 (3H,s), 3.12 (4H,m), 3.69 (4H,m), 3.72 (3H,s), 6.86–6.89 (3H,m), 7.02 (2H,d), 7.11 (1H,s), 7.35–7.52 (7H,m), 7.63 (2H,d), 10.36 (1H,bs) (70° C.) |
| 9076 | C₃₆H₃₄N₄O₃·HCl | 571(35), 196(50), 167(100), 108(80) | CI | CDCl₃/300 MHz | 2.7–4.3 (4H,m), 2.90 (3H,s), 3.05 (3H,s), 4.95 (1H,bs) 7.0–8.5 (21H,m), 9.35 (1H,bs), 11.95 (1H,bs) |
| 9079 | C₃₉H₃₈N₄O₄ | 627(5), 156(36), 85(100) | CI | d₆-DMSO/400 MHz | 1.62 (2H,m), 1.88–2.04 (2H,m), 2.40–2.82 (8H,m), 2.89 (3H,s), 4.77 (1H,s), 6.87 (1H,s), 7.09 (1H,s), 7.17–7.80 (17H,m), 8.02 (2H,d), 10.19 (1H,s) |
| 9080 | C₃₉H₃₅N₅O₃ | 622(100) | ESI | d₆-DMSO/400 MHz | 2.64–2.90 (8H,m), 2.86 (3H,s), 3.68 (2H,s), 6.88 (1H,s), 6.90–7.04 (2H,m), 7.10 (1H,s), 7.22–7.48 (9H,m), 7.72 (4H,m), 8.00 (2H,d), 10.19 (1H,s), 10.67 (1H,s) |
| 9096 | C₃₈H₃₃N₅O₃ | 608(15), 291(100) | CI | d₆-DMSO/400 MHz | 2.74 (3H,s), 2.70 (2H,m), 2.80 (2H,m), 3.58 (2H,s), 3.70 (2H,s), 6.88 (1H,s), 6.90–7.05 (2H,m), 7.10 (1H,s), 7.20–7.50 (9H,m), 7.65–7.80 (4H,m), 8.00 (2H,d), 10.27 (1H,s), 10.62 (1H,s) |
| 9103 | C₃₈H₃₇N₅O₃ | 612(87), 175(100) | CI | d₆-DMSO/400 MHz | 2.5–2.6 (6H,m), 2.75 (2H,m), 2.85 (3H,s), 3.11 (4H,m), 6.75 (1H,t), 6.88 (1H,s), 6.90 (2H,d), 7.1 (1H,s), 7.2 (3H,m), 7.28–7.49 (7H,m), 7.75 (3H,m) 8.1 (2H,d), 10.15 (1H,s), 10.6 (1H,bs) |
| 9104 | C₃₇H₃₅N₅O·HCl | 598(100) | CI | d₆-DMSO/400 MHZ | 2.5 (4H,m), 2.85 (3H,s), 3.11 (4H,m), 3.5 (2H,s), 6.75 (1H,t), 6.88 (1H,s), 6.90 (2H,d), 7.1 (1H,s), 7.2 (3H,m), 7.28–7.49 (7H,m), 7.75 (3H,m), 8.1 (2H,d) |
| 9116 | C₃₁H₃₀N₄O₃·HCl | 507(100) | CI | CDCl₃/300 MHz | 2.90 (3H,s), 3.0–4.8 (10H,m), 6.86 (1H,s), 7.11 (1H,s), 7.15–7.50 (9H,m), 7.68(2H,d), 7.96 (2H,d), 8.77 (1H,bs), 10.34 (1H,bs), 10.42 (1H,b) |
| 9117 | C₃₀H₂₉N₃O₅ | 529(5), 512(100), 275(10), 118(20) | CI | CDCl₃/300 MHz | 2.93 (2H,t), 3.05 (3H,s), 23.76 (2H,q), 3.90 (3H,s), 3.92 (3H,s), 6.20 (1H,bt), 6.81–6.90 (3H,m), 7.08 (1H,s), 7.30–7.47 (6H,m), 7.51 (2H,d), 7.81 (2H,d), 8.04 (1H,bs) |
| 9115 | C₃₂H₃₃N₃O₄ | 524(95), 190(100) | CI | d₆-DMSO/400 MHz | 2.63–2.72 (4H,m), 2.7 (3H,s), 2.84 (4H,bs), 3.52 (2H,s), 3.69 (6H,s), 6.61 (1H,s), 6.65 (1H,s), 6.8 (1H,s), 6.98 (1H,s), 7.07 (1H,s), 7.28–7.51 (9H,m) |
| 9161 | C₄₀H₄₀N₄O₅ | 657(7) | CI | CDCl₃/400 MHz | 1.92 (2H,m), 2.47–2.85 (8H,m), 2.99 (3H,s), 3.57 (2H,s), 3.85 (2x3H,s), 6.52 (1H,s), 6.59 (1H,s), 7.10 (1H,s), 7.15–7.60 (13H,m), 7.85 (1H,m), 7.98 (1H,s), 8.08 (1H,s) |
| 9083 | C₃₈H₃₇N₅O₃ | 612(100) | ESI | CDCl₃/400 MHz | 2.62–2.72 (6H,m), 2.82–2.89 (2H,m), 2.99 (3H,s), 3.25 (4H,m), 6.88 (1H,t), 6.96 (2H,d), 7.09 (1H,s), 7.20–7.29 (6H,m), 7.32–7.42 (4H,m), 7.53–7.61 (4H,m), 7.85 (1H,m), 7.97 (1H,s), 8.05 (1H,s), 8.53 (1H,bs) |
| 9128 | C₃₈H₃₆O₅N₄ | 629(100) | ESI | CDCl₃/400 MHz | 2.74 (m,2H), 2.83 (m.2H), 3.01 (s.3H), 3.55 (s,2H), 3.69 (s,2H), 3.82 (s,3H), 3.85 (s,3H), 6.49 (s,1H), 6.58 (s,1H), 7.09 (s,1H), 7.25–7.44 (10H,m), 7.58–7.64 (4H,m), 7.92 (1H,s), 7.96 (1H,s) |
| 9136 | C₃₃H₃₄N₄O₅ | 567(100) | CI | CDCl₃/400 MHz | 2.75–2.90 (6H,m), 3.00 (3H,s), 3.60–3.72 (4H,m), 3.84 (6H,s), 6.54 (1H,s), 6.60 (1H,s), 7.03–7.11 (2H,m), 7.24–7.78 (10H,m), 7.84 (1H,s) |
| 9137 | C₃₃H₃₆N₄O₅ | 569(95), 357(100) | CI | CDCl₃/400 MHz | 2.38 (3H,s), 2.62–2.80 (6H,m), 3.2 (3H,s), 3.46–3.54 (2H,m), 3.75 (3H,s), 3.81 (3H,s), 6.60–6.85 (5H,m), 7.6 (1H,s), 7.25–7.55 (9H,m) 7.79 (1H,s) |
| 9138 | C₃₉H₄₀N₄O₅ | 645(71), 106(100) | CI | CDCl₃/400 MHz | 2.38 (3H,s), 2.60–2.82 (8H,m), 2.96 (3H,s), 3.85 (2x3H,s), 6.68–6.82 (3H,m), 7.04–7.60 (14H,m), 7.81 (1H,d), 7.97 (1H,s), 8.07 (1H,s) |
| 9155 | C₃₇H₃₆N₄O₅S | 649(100) | ESI | CDCl₃/400 MHz | 2.72–2.93 (8H,m), 3.19 (3H,s), 3.65 (2H,s), 3.85 (2x3H,s), 6.54 (1H,s), 6.60 (1H,s), |

TABLE 10-continued

| | | Mass spec data | | $^1$H nmr data | |
|---|---|---|---|---|---|
| No. | Mol. Formula | mass (intensity) | mode | solvent/field | δ |
| 9163 | $C_{37}H_{36}N_4O_3$ | 585(100) | ESI | CDCl$_3$/400 MHz | 7.04 (1H,m), 7.08–7.10 (2H,m), 7.22–7.29 (3H,m), 7.45 (1Hm), 7.52–7.60 (4H,m), 7.81 (1H,m), 7.95 (2H,s) 8.38 (1H,s) 2.36(3H,s), 2.65 (2H,t), 2.95–3.10 (5H,m), 3.45 (2H,d), 4.20 (1H,t), 6.38 (1H,brs), 7.05–8.20 (22H,m) |
| 9176 | | | | CDCl$_3$/400 MHz | 2.70–2.98 (8H,m), 3.00 (3H,s), 3.65 (2H,s), 3.82 (2x3H,s), 5.09 (2H,s), 6.53 (1H,s), 6.61 (1H,s), 7.00–7.10 (4H,m), 7.21–7.58 (7H,m), 7.82 (2H,d), 7.91 (1H,br s) |
| 9177 | | | | CDCl$_3$/400 MHz | 2.62–2.89 (8H,m), 2.91 (3H,s), 3.57 (2H,s), 3.76 (2x3H,s), 4.97 (2H,s), 6.45 (1H,s), 6.51 (1H,s), 6.82–6.95 (3H,m), 7.12–7.38 (12H,m), 8.05 (1H,br s) |
| 9190 | $C_{39}H_{38}N_4O_3$ | 643(3) | CI | CDCl$_3$/400 MHz | 2.70–3.04 (11H,m), 3.65 (2H,s), 3.85 (2x3H,s), 6.53 (1H,s), 6.60 (1H,s), 7.03 (1H,s), 7.15–7.50 (11H,m), 7.68–7.92 (5H,m) |
| 9200 | $C_{37}H_{40}N_4O_5$ | 620(32) | EI | CDCl$_3$/400 MHz | 1.05–2.00 (9H,m), 2.35–2.45(2Hd), 2.62–2.84 (4H,m), 3.2 (3H,s), 3.55 (2H,s), 3.84 (2x3H,s), 6.52 (1H,s), 6.60 (1H,s), 7.06 (1H,s), 7.20–7.55 (11H,m) |

We claim:

1. A piperazinedione of general formula (I):

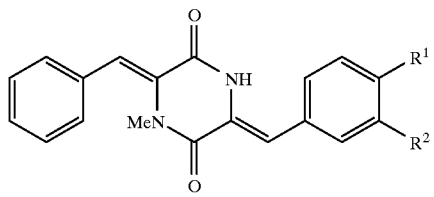
(I)

wherein $R^1$ is selected from:

hydrogen a group of formula —(NH)$_t$—COR$^3$ wherein t is 0 and R$^3$ is selected from:

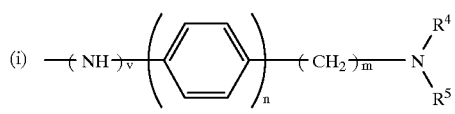
(A)

wherein v is 1; and wherein n is 0 or 1 and m is 0, 1, 2 or 3, at least one of n and m being other than 0, and either (a) R$^4$ is H or C$_1$–C$_6$ alkyl and R$^5$ is C$_1$–C$_6$ alkyl optionally substituted by one or two phenyl groups, the phenyl group or groups being optionally substituted by one or two C$_1$–C$_6$ alkoxy groups; or (b) R$^4$ and R$^5$, together with the nitrogen atom to which they are attached, form a heterocyclic group selected from (1) to (4):

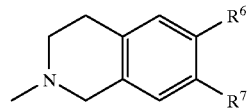
(1)

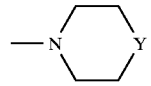
(2)

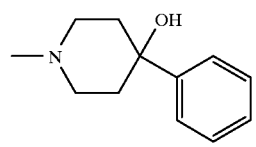
(3)

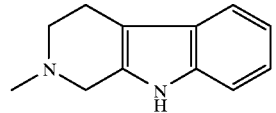
(4)

wherein R$^6$ and R$^7$, which are the same or different, are H or C$_1$–C$_6$ alkoxy, or R$^6$ and R$^7$ together form a methylenedioxy group; Y is O or —NR$^8$ wherein R$^8$ is C$_1$–C$_6$ alkyl or a phenyl group optionally substituted by CF$_3$;

—NH—(CH$_2$)$_p$—Z (B)

wherein p is 1 or 2 and Z is C$_2$–C$_6$ alkenyl or a phenyl group optionally substituted by C$_1$–C$_6$ alkoxy; and

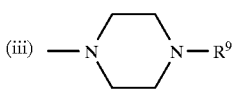

(C)

wherein $R^9$ is $C_1$–$C_6$ alkyl, pyrimidinyl or a phenyl group optionally substituted by $C_1$–$C_6$ alkoxy;

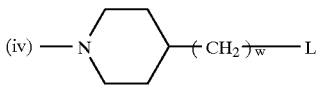

(F)

or $R^1$ is selected from:
a group of the formula (D):

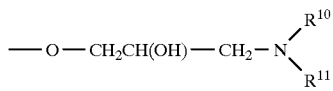

(D)

wherein each of $R^{10}$ and $R^{11}$, which may be the same or different, is $C_1$–$C_6$ alkyl; and
a group of formula (E):

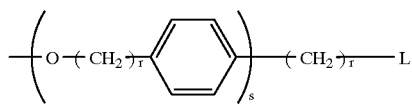

(E)

wherein s is 0, r is 1, 2 or 3 and L is a heterocyclic group of formula (1) as defined above; and $R^2$ is hydrogen or a group of formula —$COR^3$ as defined above, provided that one of $R^1$ and $R^2$ is hydrogen and the other is not hydrogen; or a pharmaceutically acceptable salt thereof.

2. A compound according to claim 1 wherein $R^1$ is hydrogen and $R^2$ is a group of formula —$COR^3$ as defined in claim 1 in which $R^3$ is a group of formula A.

3. A compound according to claim 1, wherein $R^2$ is hydrogen and $R^1$ is a group of formula —$COR^3$ as defined in claim 1 in which $R^3$ is a group of formula (A), a group of formula (B) wherein Z is ethenyl or phenyl substituted by two $C_1$–$C_6$ alkoxy groups, or a group of formula (C) wherein $R^9$ is methyl, pyrimidinyl or phenyl.

4. A compound according to claim 1 wherein, in formula (A), n is 0 and m is 2, or n is 1 and m is 0, 1, 2 or 3, or n is 1 and m is 0, and either
 (a) $R^4$ is $C_1$–$C_6$ alkyl and $R^5$ is $C_1$–$C_6$ alkyl substituted on the terminal C atom by 2 unsubstituted phenyl groups or by one phenyl group which is disubstituted by $C_1$–$C_6$ alkoxy groups; or
 (b) $R^4$ and $R^5$ form together with the nitrogen atom to which they are attached a heterocyclic group selected from groups of formula (1) wherein $R^6$ and $R^7$ are both H or both $C_1$–$C_6$ alkoxy, or together form a methylenedioxy group; formula (2) wherein Y is O or —$NR^8$ wherein $R^8$ is methyl, phenyl or trifluoromethylphenyl; formula (3); and formula (4).

5. A compound according to claim 1 wherein $R^2$ is hydrogen and $R^1$ is a group of formula (D) or (E) as defined in claim 1.

6. A compound selected from:
1-(4-((3Z,6Z)-6-Benzylidene-1-methyl-2,5-dioxo-3-piperazinylidene)methylbenzoyl)-4-(2-pyrimidyl)piperazine (9022);
1-(4-((3Z,6Z)-6-Benzylidene-1-methyl-2,5-dioxo-3-piperazinylidene)methylbenzoyl)-4-methylpiperazine, hydrochloride (9052);
1-(4-((3Z,6Z)-6-Benzylidene-1-methyl-2,5-dioxo-3-piperazinylidene)methylbenzoyl)-4-(4-methoxyphenyl)piperazine, hydrochloride (9071);
N-Allyl-4-((3Z,6Z)-6-benzylidene-1-methyl-2,5-dioxo-3-piperazinylidene)methylbenzamide (9070);
N-(2-Diphenylmethylmethylaminoethyl)-4-((3Z,6Z)-6-benzylidene-1-methyl-2,5-dioxo-3-piperazinylidene)methylbenzamide, hydrochloride (9076);
N-(2-(1,2,3,4-Tetrahydro-2-isoquinloyl)ethyl)-4-((3Z,6Z)-6-benzylidene-1-methyl-2,5-dioxo-3-piperazinylidene)methylbenzamide, hydrochloride (9116);
N-(3,4-Dimethoxyphenethyl)-4-((3Z,6Z)-6-benzylidene-1-methyl-2,5-dioxo-3-piperazinylidene)methylbenzamide (9117);
N-(4-(4-Phenyl-1-piperazinyl)methylphenyl)-4-((3Z,6Z)-6-benzylidene-1-methyl-2,5-dioxo-3-piperazinylidene)methylbenzamide, hydrochloride (9104);
N-(2-(4-Methyl-1-piperazinyl)ethyl)-4-((3Z,6Z)-6-benzylidene-1-methyl-2,5-dioxo-3-piperazinylidene)methylbenzamide (9007);
N-(2-Morpholinoethyl)-4-((3Z,6Z)-6-benzylidene-1-methyl- 2,5-dioxo-3-piperazinylidene)methylbenzamide, hydrochloride (9053);
N-(4-Morpholinophenyl)-4-((3Z,6Z)-6-benzylidene-1-methyl-2,5-dioxo-3-piperazinylidene)methylbenzamide, hydrochloride (9054);
N-(4-(2-(1,2,3,4-Tetrahydro-β-carbolin-2-yl)ethyl)phenyl)-4-((3Z,6Z)-6-benzylidene-1-methyl-2,5-dioxo-3-piperazinylidene)methylbenzamide (9080);
N-(4-(1,2,3,4-Tetrahydro-β-carbolin-2-yl)methylphenyl)-4-(3Z,6Z)-6-benzylidene-1-methyl-2,5-dioxo-3-piperazinylidene)methylbenzamide (9096);
N-(4-(2-(4-Phenyl-1-piperazinyl)ethyl)phenyl)-4-((3Z,6Z)-6-benzylidene-1-methyl-2,5-dioxo-3-piperazinylidene)methylbenzamide (9103);
N-(4-(2-(1,2,3,4-Tetrahydro-2-isoquinolyl)ethyl)phenyl)-4-((3Z,6Z)-6-benzylidene-1-methyl-2,5-dioxo-3-piperazinylidene)methylbenzamide (9065);
N-(4-(2-(4-(3-Trifluoromethylphenyl)-1-piperazinyl)ethyl)phenyl)-4-((3Z,6Z)-6-benzylidene-1-methyl-2,5-dioxo-3-piperazinylidene)methylbenzamide (9049);
N-(4-(2-(6,7-Dimethoxy-1,2,3,4-tetrahydro-2-isoquinolyl)ethyl)phenyl)-4-((3Z,6Z)-6-benzylidene-1-methyl-2,5-dioxo-3-piperazinylidene)methylbenzamide (9006);
N-(2-(6,7-Dimethoxy-1,2,3,4-tetrahydro-2-isoquinolyl)ethyl)-4-((3Z,6Z)-6-benzylidene-1-methyl-2,5-dioxo-3-piperazinylidene)methylbenzamide (9008);
N-(4-(6,7-Dimethoxy-1,2,3,4-tetrahydro-2-isoquinolyl)methylphenyl)-4-((3Z,6Z)-6-benzylidene-1-methyl-2,5-dioxo-3-piperazinylidene)methylbenzamide, hydrochloride (9064);
(3Z,6Z)-6-Benzylidene-3-(4-(3-dimethylamino-2-hydroxypropoxy)benzylidene)-1-methyl-2,5-piperazinedione (9023);
(3Z,6Z)-6-Benzylidene-3-(4-(2-(6,7-dimethoxy-1,2,3,4-tetrahydro-2-isoquinolyl)ethyl)benzylidene)-1-methyl-2,5-piperazinedione (9115);
N-(4-(2-(6,7-Dimethoxy-1,2,3,4-tetrahydro-2-isoquinolyl)ethyl)phenyl)-3-((3Z,6Z)-6-benzylidene- 1-methyl-2,5-dioxo-3-piperazinylidene)methylbenzamide, hydrochloride (9051);

N-(4-(6,7-Dimethoxy-1,2,3,4-tetrahydro-2-isoquinolyl)
methylphenyl)-3-((3Z,6Z)-6-benzylidene-1-methyl-2,5-
dioxo-3-piperazinylidene)methylbenzamide (9128);

N-(2-(6,7-Dimethoxy-1,2,3,4-tetrahydro-2-isoquinolyl)
ethyl)-3-((3Z,6Z)-6-benzylidene-1-methyl-2,5-dioxo-3-
piperazinylidene)methylbenzamide (9136);

N-(2-(3,4-Dimethoxyphenethyl)methylamino)ethyl)-3-
((3Z,6Z)-6-benzylidene-1-methyl-2,5-dioxo-3-
piperazinylidene)methylbenzamide (9137);

N-(4-(2-((3,4-Dimethoxyphenethyl)methylamino)ethyl)
phenyl)-3-((3Z,6Z)-6-benzylidene-1-methyl-2,5-dioxo-3-
piperazinylidene)methylbenzamide (9138);

N-(4-(2-(4-Phenyl-1-piperazinyl)ethyl)phenyl)-3-((32,6Z)-
6-benzylidene-1-methyl-2,5-dioxo-3-piperazinylidene)
methylbenzamide (9083);

N-(4-(3-(6,7-Dimethoxy-1,2,3,4-tetrahydro-2-isoquinolyl)
propyl)phenyl)-3-((3Z,6Z)-6-benzylidene-1-methyl-2,5-
dioxo-3-piperazinylidene)methylbenzamide, hydrochloride (9161);

N-(2-(2,2-Diphenylethyl)methylaminoethyl)-3-((3Z,6Z)-6-
benzylidene-1-methyl-2,5-dioxo-3-piperazinylidene)
methylbenzamide (9163);

(3Z,6Z)-6-Benzylidene-3-(4-(4-(2-(6,7-dimethoxy-1,2,3,4-
tetrahydro-2-isoquinolyl)ethyl)benzyloxy)benzylidene)-
1-methyl-2,5-piperazinedione (9176);

N-(4-((3Z,6Z)-6-Benzylidene-1-methyl-2,5-dioxo-3-
piperazinylidene)methylphenyl)-4-(2-(6,7-dimethoxy-1,
2,3,4-tetrahydro-2-isoquinolyl)ethyl)benzamide (9190).

7. A piperazinedione of general formula (I):

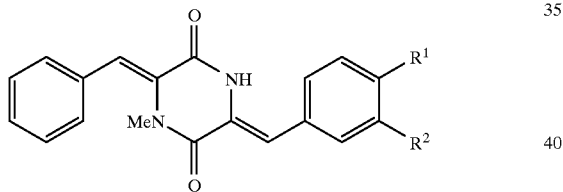

(I)

wherein $R^1$ is selected from:

hydrogen; and a group of formula —(NH)$_t$—COR$^3$ wherein t is 1 and $R^3$ is selected from:

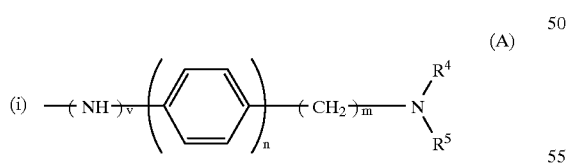

(A)

wherein v is 0; and wherein n is 0 or 1 and m is 0, 1, 2 or 3, at least one of n and m being other than 0, and either (a) $R^4$ is H or $C_1$–$C_6$ alkyl and $R^5$ is $C_1$–$C_6$ alkyl optionally substituted by one or two phenyl groups, the phenyl group or groups being optionally substituted by one or two $C_1$–$C_6$ alkoxy groups; or (b) $R^4$ and $R^5$, together with the nitrogen atom to which they are attached, form a heterocyclic group selected from (1) to (4):

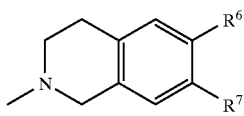

(1)

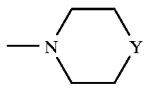

(2)

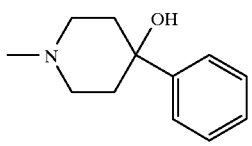

(3)

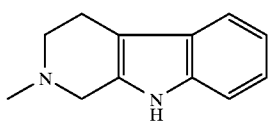

(4)

wherein $R^6$ and $R^7$, which are the same or different, are H or $C_1$–$C_6$ alkoxy, or $R^6$ and $R^7$ together form a methylenedioxy group; Y is O or —NR$^8$ wherein $R^8$ is $C_1$–$C_6$ alkyl or a phenyl group optionally substituted by $CF_3$;

—NH—(CH$_2$)$_p$—Z  (B)

wherein p is 1 or 2 and Z is $C_2$–$C_6$ alkenyl or a phenyl group optionally substituted by $C_1$–$C_6$ alkoxy; and (C)

(iii) 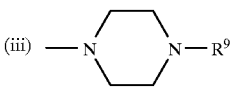

wherein $R^9$ is $C_1$–$C_6$alkyl, pyrimidinyl or a phenyl group optionally substituted by $C_1$–$C_6$ alkoxy; and (F)

(iv) 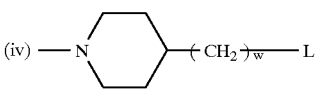

wherein w is 1, 2 or 3 and L is a heterocyclic group of formula (1) as defined above; or $R^1$ is selected from a group of the formula (D):

(D)

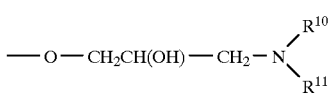

wherein each of $R^{10}$ and $R^{11}$, which may be the same or different, is $C_1$–$C_6$ alkyl; and a group of formula (E):

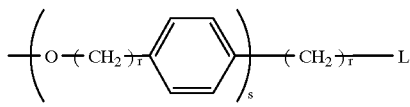

wherein s is 0 or 1 and each r, which may be the same or different, is 1, 2 or 3 and L is a heterocyclic group of formula (1) as defined above; and $R^2$ is hydrogen or a group of formula —$(NH)_t$—$COR^3$ as defined above, provided that one of $R^1$ and $R^2$ is hydrogen and the other is not hydrogen; or a pharmaceutically acceptable salt thereof.

8. A compound according to claim 7 wherein $R^1$ is hydrogen and $R^2$ is a group of formula —$(NH)_t$—$COR^3$ in which $R^3$ is a group of formula A.

9. A compound according to claim 7 wherein $R^2$ is hydrogen and $R^1$ is a group of formula —$(NH)_t$—$COR^3$ in which $R^3$ is a group of formula —$(NH)_t$—$COR^3$ in which $R^3$ is a group of formula (A), a group of formula (B) wherein Z is ethenyl or phenyl substituted by two $C_1$–$C_6$ alkoxy groups, or a group of formula (C) wherein $R^9$ is methyl, pyrimidinyl or phenyl.

10. A compound according to claim 7, wherein, in formula (A), n is 0 and m is 2, or n is 1 and m is 0, 1, 2 or 3, or n is 1 and m is 0, and either
   (a) $R^4$ is $C_1$–$C_6$ alkyl and $R^5$ is $C_1$–$C_6$ alkyl substituted on the terminal C atom by 2 unsubstituted phenyl groups or by one phenyl group which is disubstituted by $C_1$–$C_6$ alkoxy groups; or
   (b) $R^4$ and $R^5$ form together with the nitrogen atom to which they are attached a heterocyclic group selected from groups of formula (1) wherein $R^6$ and $R^7$ are both H or both $C_1$–$C_6$ alkoxy, or together form a methylenedioxy group; formula (2) wherein Y is O or —$NR^8$ wherein $R^8$ is methyl, phenyl or trifluoromethylphenyl; formula (3); and formula (4).

11. A compound according to claim 7 wherein $R^2$ is hydrogen and $R^1$ is a group of formula (D) or (E) as defined in claim 7.

12. A pharmaceutical or veterinary composition which comprises a pharmaceutically or veterinarily acceptable carrier or diluent and, as an active principal, a compound as claimed in claim 7.

13. A process for producing a compound as defined in claim 7, which process comprises treating 1-acetyl-3-benzylidene-4-methyl-2,5-piperazinedione with an aldehyde of formula (III):

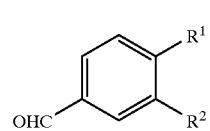

wherein $R^1$ and $R^2$ are as defined in claim 1 or 7, in an organic solvent in the presence of a base; and, if desired, converting the resulting compound into a pharmaceutically acceptable salt thereof.

14. A method of treating resistance to a chemotherapeutic agent in a patient harboring a tumor which method comprises administering to a patient in need thereof a therapeutically effective amount of a compound as defined in claim 1 or 7 wherein the chemotherapeutic agent is selected from the group consisting of anthracyline antibiotics, vinca alkaloids, mitoxantrone, actinomycin D, taxanes, epipodophyllotoxins and plicamycin.

15. A method according to claim 14 wherein the chemotherapeutic agent is an anthracycline antiobiotic.

16. A method according to claim 15 wherein the anthracycline antibiotic is doxorubicin or daunorubicin.

17. A method according to claim 14, which comprises administering the said compound to the patient whilst the tumor is exposed to the said chemotherapeutic agent.

18. A method of modulating P-gp mediated MDR in the treatment of tumors, which method comprises administering to a patient harboring a tumor which expresses P-gp mediated MDR a therapeutically effective amount of a compound as defined in claim 1 or 7.

* * * * *